United States Patent
Bedford et al.

(10) Patent No.: US 6,562,340 B1
(45) Date of Patent: *May 13, 2003

(54) ENZYME FEED ADDITIVE AND ANIMAL FEED INCLUDING IT

(75) Inventors: Michael R. Bedford, Marlborough (GB); Andrew J. Morgan, Marlborough (GB); Timothy Fowler, Belmont, CA (US); Kathleen A. Clarkson, San Francisco, CA (US); Michael Ward, San Francisco, CA (US); Katherine D. Collier, Redwood City, CA (US); Edmund A Larenas, San Carlos, CA (US)

(73) Assignee: Genencor International, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/507,362

(22) PCT Filed: Dec. 19, 1994

(86) PCT No.: PCT/EP94/04212

§ 371 (c)(1),
(2), (4) Date: Oct. 27, 1995

(87) PCT Pub. No.: WO95/16360

PCT Pub. Date: Jun. 22, 1995

Related U.S. Application Data

(63) Continuation of application No. 08/169,948, filed on Dec. 17, 1993, now Pat. No. 5,861,271.

(51) Int. Cl.[7] .................. A61K 38/47; A61K 38/43; A61K 38/54; A23K 1/00
(52) U.S. Cl. ................ 424/94.61; 424/94.1; 424/94.2; 426/615
(58) Field of Search .................... 424/94.61, 94.1, 424/94.2; 426/615

(56) References Cited

U.S. PATENT DOCUMENTS

| 5,536,655 A | * | 7/1996 | Thomas et al. | 435/209 |
| 5,753,484 A | * | 5/1998 | Ward et al. | 435/209 |
| 5,874,276 A | * | 2/1999 | Fowler et al. | 435/209 |

FOREIGN PATENT DOCUMENTS

| WO | 9009436 | * | 8/1990 |

(List continued on next page.)

OTHER PUBLICATIONS

Bedford J. of the Science of Food & Agriculture 63(1):107–108, 1993.*

(List continued on next page.)

*Primary Examiner*—Mary K. Zeman
*Assistant Examiner*—Lori A. Clow
(74) *Attorney, Agent, or Firm*—Genencor International, Inc

(57) ABSTRACT

The use is provided of a composition as a feed additive which comprises one or more endoglucanases, and 0–20% by weight, based upon the content of cellulase proteins in the composition, of a cellobiohydrolase. The endoglycanases may be one or more of EGI, EGII EGIII and any functionally active derivative of any thereof. Such endoglucanases may be obtained from a genetically modified strain of the fungus Trichoderma. Also provided is an enzyme-based feed additive which comprises EGI and/or EGII which lack the cellulose binding domain, and 0–20% by weight, based upon the content of cellulase proteins in the additive, of a cellobiohydrolase. A further enzyme-based feed additive is provided which comprises a cereal-based carrier, one or more endoglucanases, and 0–20% by weight, based upon the content of cellulase proteins in the additive, of a cellobiohydrolase. Such enzyme-based feed additives can be incorporated into a cereal-based feed which includes one or more of barley, wheat, tricale, rye and maize. The feed additive has the advantage of improving the feed conversion ratio and/or increasing the digestibility of a cereal-based feed in which it is included.

21 Claims, 11 Drawing Sheets

FOREIGN PATENT DOCUMENTS

| WO | 9104673 | * | 4/1991 |
| WO | 9118090 | * | 11/1991 |
| WO | 9320714 | * | 10/1993 |

OTHER PUBLICATIONS

Bedford et al. J. of the Science of Food & Agriculture 63(1): 107–108, 1993.*

Durrant et al. J. Biochem. (England 273 Pt 2: 289–293, 1991.*

Langsford et al. FEB Letter 05364 vol. 225, No. 1,2: 163–167, 1987.*

Saloheimo et al. Mol. Microbiol. 13 (2) : 219–228, 1994.*

J. Rudinger "Characteristics of the amino acids as components of a peptide hormone sequence," In: Peptide Hormones, Parsons, ed., Univeristy Park Press, Baltimore, 1976, pp. 1–7, 1976.*

* cited by examiner

```
TGTGTTGAAATCCAACTTATAAAGACAACAACCGCAAACTTTGTCTTGTG
├─────────┼─────────┼─────────┼─────────┼─────────┤ 50
CCATCAGATTGTTGCCAAGCACCGTCCCCCCCCCTATCTTAGTCCTTCT
├─────────┼─────────┼─────────┼─────────┼─────────┤ 100
TGTTGTCCCAAAATGGCGCCCTCAGTTACACTGCCGTTGACCACGGCCAT
├─────────┼─────────┼─────────┼─────────┼─────────┤ 150
              Met Ala Pro Ser Val Thr Leu Pro Leu Thr Thr Ala Ile
CCTGGCCATTGCCCGGCTCGTCGCCGCCCAGCAACCGGGTACCAGCACCC
├─────────┼─────────┼─────────┼─────────┼─────────┤ 200
 Leu Ala Ile Ala Arg Leu Val Ala Ala Gln Gln Pro Gly Thr Ser Thr
CCGAGGTCCATCCCAAGTTGACAACCTACAAGTGTACAAAGTCCGGGGGG
├─────────┼─────────┼─────────┼─────────┼─────────┤ 250
Pro Glu Val His Pro Lys Leu Thr Thr Tyr Lys Cys Thr Lys Ser Gly Gly
 TGCGTGGCCCAGGACACCTCGGTGGTCCTTGACTGGAACTACCGCTGGAT
├─────────┼─────────┼─────────┼─────────┼─────────┤ 300
 Cys Val Ala Gln Asp Thr Ser Val Val Leu Asp Trp Asn Tyr Arg Trp Met
GCACGACGCAAACTACAACTCGTGCACCGTCAACGGCGGCGTCAACACCA
├─────────┼─────────┼─────────┼─────────┼─────────┤ 350
     His Asp Ala Asn Tyr Asn Ser Cys Thr Val Asn Gly Gly Val Asn Thr
CGCTCTGCCCTGACGAGGCGACCTGTGGCAAGAACTGCTTCATCGAGGGC
├─────────┼─────────┼─────────┼─────────┼─────────┤ 400
Thr Leu Cys Pro Asp Glu Ala Thr Cys Gly Lys Asn Cys Phe Ile Glu Gly
GTCGACTACGCCGCCTCGGGCGTCACGACCTCGGGCAGCAGCCTCACCAT
├─────────┼─────────┼─────────┼─────────┼─────────┤ 450
 Val Asp Tyr Ala Ala Ser Gly Val Thr Thr Ser Gly Ser Ser Leu Thr Met
GAACCAGTACATGCCCAGCAGCTCTGGCGGCTACAGCAGCGTCTCTCCTC
├─────────┼─────────┼─────────┼─────────┼─────────┤ 500
 Asn Gln Tyr Met Pro Ser Ser Ser Gly Gly Tyr Ser Ser Val Ser Pro
GGCTGTATCTCCTGGACTCTGACGGTGAGTACGTGATGCTGAAGCTCAAC
├─────────┼─────────┼─────────┼─────────┼─────────┤ 550
Arg Leu Tyr Leu Leu Asp Ser Asp Gly Glu Tyr Val Met Leu Lys Leu Asn
GGCCAGGAGCTGAGCTTCGACGTCGACCTCTCTGCTCTGCCGTGTGGAGA
├─────────┼─────────┼─────────┼─────────┼─────────┤ 600
 Gly Gln Glu Leu Ser Phe Asp Val Asp Leu Ser Ala Leu Pro Cys Gly Glu
GAACGGCTCGCTCTACCTGTCTCAGATGGACGAGAACGGGGGCGCCAACC
├─────────┼─────────┼─────────┼─────────┼─────────┤ 650
     Asn Gly Ser Leu Tyr Leu Ser Gln Met Asp Glu Asn Gly Gly Ala Asn
AGTATAACACGGCCGGTGCCAACTACGGGAGCGGCTACTGCGATGCTCAG
├─────────┼─────────┼─────────┼─────────┼─────────┤ 700
Gln Tyr Asn Thr Ala Gly Ala Asn Tyr Gly Ser Gly Tyr Cys Asp Ala Gln
TGCCCCGTCCAGACATGGAGGAACGGCACCCTCAACACTAGCCACCAGGG
├─────────┼─────────┼─────────┼─────────┼─────────┤ 750
 Cys Pro Val Gln Thr Trp Arg Asn Gly Thr Leu Asn Thr Ser His Gln Gly
CTTCTGCTGCAACGAGATGGATATCCTGGAGGGCAACTCGAGGGCGAATG
├─────────┼─────────┼─────────┼─────────┼─────────┤ 800
 Phe Cys Cys Asn Glu Met Asp Ile Leu Glu Gly Asn Ser Arg Ala Asn
```

*FIG. 1A*

```
CCTTGACCCCTCACTCTTGCACGGCCACCGCCTGCGACTCTGCCGGTTGC
                                                    850
 Ala Leu Thr Pro His Ser Cys Thr Ala Thr Ala Cys Asp Ser Ala Gly Cys
GGCTTCAACCCCTATGGCAGCGGCTACAAAAGGTGAGCCTGATGCCACTA
                                                    900
 Gly Phe Asn Pro Tyr Gly Ser Gly Tyr Lys Ser
CTACCCCTTTCCTGGCGCTCTCGCGGTTTTCCATGCTGACATGGTTTTCC
                                                    950

AGCTACTACGGCCCCGGAGATACCGTTGACACCTCCAAGACCTTCACCAT
                                                    1000
  — Tyr Tyr Gly Pro Gly Asp Thr Val Asp Thr Ser Lys Thr Phe Thr Ile
CATCACCCAGTTCAACACGGACAACGGCTCGCCCTCGGGCAACCTTGTGA
                                                    1050
 Ile Thr Gln Phe Asn Thr Asp Asn Gly Ser Pro Ser Gly Asn Leu Val
GCATCACCCGCAAGTACCAGCAAAACGGCGTCGACATCCCCAGCGCCCAG
                                                    1100
 Ser Ile Thr Arg Lys Tyr Gln Gln Asn Gly Val Asp Ile Pro Ser Ala Gln
CCCGGCGGCGACACCATCTCGTCCTGCCCGTCCGCCTCAGCCTACGGCGG
                                                    1150
 Pro Gly Gly Asp Thr Ile Ser Ser Cys Pro Ser Ala Ser Ala Tyr Gly Gly
CCTCGCCACCATGGGCAAGGCCCTGAGCAGCGGCATGGTGCTCGTGTTCA
                                                    1200
  Leu Ala Thr Met Gly Lys Ala Leu Ser Ser Gly Met Val Leu Val Phe
GCATTTGGAACGACAACAGCCAGTACATGAACTGGCTCGACAGCGGCAAC
                                                    1250
 Ser Ile Trp Asn Asp Asn Ser Gln Tyr Met Asn Trp Leu Asp Ser Gly Asn
GCCGGCCCCTGCAGCAGCACCGAGGGCAACCCATCCAACATCCTGGCCAA
                                                    1300
  Ala Gly Pro Cys Ser Ser Thr Glu Gly Asn Pro Ser Asn Ile Leu Ala Asn
CAACCCCAACACGCACGTCGTCTTCTCCAACATCCGCTGGGGAGACATTG
                                                    1350
  Asn Pro Asn Thr His Val Val Phe Ser Asn Ile Arg Trp Gly Asp Ile
GGTCTACTACGAACTCGACTGCGCCCCCGCCCCCGCCTGCGTCCAGCACG
                                                    1400
 Gly Ser Thr Thr Asn Ser Thr Ala Pro Pro Pro Pro Ala Ser Ser Thr
ACGTTTTCGACTACACCGAGGAGCTCGACGACTTCGAGCAGCCCGAGCTG
                                                    1450
 Thr Phe Ser Thr Thr Pro Arg Ser Ser Thr Thr Ser Ser Ser Pro Ser Cys
CACGCAGACTCACTGGGGGCAGTGCGGTGGCATTGGGTACAGCGGGTGCA
                                                    1500
  Thr Gln Thr His Trp Gly Gln Cys Gly Gly Ile Gly Tyr Ser Gly Cys
AGACGTGCACGTCGGGCACTACGTGCCAGTATAGCAACGACTGTTCGTAT
                                                    1550
 Lys Thr Cys Thr Ser Gly Thr Thr Cys Gln Tyr Ser Asn Asp
```

*FIG. 1B*

```
CCCCATGCCTGACGGGAGTGATTTTGAGATGCTAACCGCTAAAATACAGA
|---|---|---|---|---|---|---|---|---|---| 1600
                                              Tyr
CTACTCGCAATGCCTTTAGAGCGTTGACTTGCCTCTGGTCTGTCCAGACG
|---|---|---|---|---|---|---|---|---|---| 1650
Tyr Ser Gln Cys Leu •
GGGGCACGATAGAATGCGGGCACGCAGGGA
|---|---|---|---|---|---→ 1680
```

```
TGCCATTTCTGACCTGGATAGGTTTTCCTATGGTCATTCCTATAAGAGAC
|-------------------------------------------------| 50

ACGCTCTTTCGTCGGCCCGTAGATATCAGATTGGTATTCAGTCGCACAGA
|-------------------------------------------------| 100

CGAAGGTGAGTTGATCCTCCAACATGAGTTCTATGAGCCCCCCCCTTGCC
|-------------------------------------------------| 150

CCCCCCCGTTCACCTTGACCTGCAATGAGAATCCCACCTTTTACAAGAGC
|-------------------------------------------------| 200

ATCAAGAAGTATTAATGGCGCTGAATAGCCTCTGCTCGATAATATCTCCC
|-------------------------------------------------| 250

CGTCATCGACAATGAACAAGTCCGTGGCTCCATTGCTGCTTGCAGCGTCC
|-------------------------------------------------| 300

Met Asn Lys Ser Val Ala Pro Leu Leu Leu Ala Ala Ser
ATACTATATGGCGGCGCCGTCGCACAGCAGACTGTCTGGGGCCAGTGTGG
|-------------------------------------------------| 350

Ile Leu Tyr Gly Gly Ala Val Ala Gln Gln Thr Val Trp Gly Gln Cys Gly
AGGTATTGGTTGGAGCGGACCTACGAATTGTGCTCCTGGCTCAGCTTGTT
|-------------------------------------------------| 400

Gly Ile Gly Trp Ser Gly Pro Thr Asn Cys Ala Pro Gly Ser Ala Cys
CGACCCTCAATCCTTATTATGCGCAATGTATTCCGGGAGCCACTACTATC
|-------------------------------------------------| 450

Ser Thr Leu Asn Pro Tyr Tyr Ala Gln Cys Ile Pro Gly Ala Thr Thr Ile
ACCACTTCGACCCGGCCACCATCCGGTCCAACCACCACCACCAGGGCTAC
|-------------------------------------------------| 500

Thr Thr Ser Thr Arg Pro Pro Ser Gly Pro Thr Thr Thr Thr Arg Ala Thr
CTCAACAAGCTCATCAACTCCACCCACGAGCTCTGGGGTCCGATTTGCCG
|-------------------------------------------------| 550

Ser Thr Ser Ser Ser Thr Pro Pro Thr Ser Ser Gly Val Arg Phe Ala
GCGTTAACATCGCGGGTTTTGACTTTGGCTGTACCACAGAGTGAGTACCC
|-------------------------------------------------| 600

Gly Val Asn Ile Ala Gly Phe Asp Phe Gly Cys Thr Thr Asp
TTGTTTCCTGGTGTTGCTGGCTGGTTGGGCGGGTATACAGCGAAGCGGAC
|-------------------------------------------------| 650

GCAAGAACACCGCCGGTCCGCCACCATCAAGATGTGGGTGGTAAGCGGCG
|-------------------------------------------------| 700

GTGTTTTGTACAACTACCTGACAGCTCACTCAGGAAATGAGAATTAATGG
|-------------------------------------------------| 750

AAGTCTTGTTACAGTGGCACTTGCGTTACCTCGAAGGTTTATCCTCCGTT
|-------------------------------------------------| 800

Gly Thr Cys Val Thr Ser Lys Val Tyr Pro Pro Leu
GAAGAACTTCACCGGCTCAAACAACTACCCCGATGGCATCGGCCAGATGC
|-------------------------------------------------| 850

Lys Asn Phe Thr Gly Ser Asn Asn Tyr Pro Asp Gly Ile Gly Gln Met
```

*FIG. 2A*

```
                AGCACTTCGTCAACGAGGACGGGATGACTATTTTCCGCTTACCTGTCGGA
                                                                    900
  Gln His Phe Val Asn Glu Asp Gly Met Thr Ile Phe Arg Leu Pro Val Gly
                TGGCAGTACCTCGTCAACAACAATTTGGGCGGCAATCTTGATTCCACGAG
                                                                    950
  Trp Gln Tyr Leu Val Asn Asn Asn Leu Gly Gly Asn Leu Asp Ser Thr Ser
                CATTTCCAAGTATGATCAGCTTGTTCAGGGGTGCCTGTCTCTGGGCGCAT
                                                                   1000
  Ile Ser Lys Tyr Asp Gln Leu Val Gln Gly Cys Leu Ser Leu Gly Ala
                ACTGCATCGTCGACATCCACAATTATGCTCGATGGAACGGTGGGATCATT
                                                                   1050
  Tyr Cys Ile Val Asp Ile His Asn Tyr Ala Arg Trp Asn Gly Gly Ile Ile
                GGTCAGGGCGGCCCTACTAATGCTCAATTCACGAGCCTTTGGTCGCAGTT
                                                                   1100
  Gly Gln Gly Gly Pro Thr Asn Ala Gln Phe Thr Ser Leu Trp Ser Gln Leu
                GGCATCAAAGTACGCATCTCAGTCGAGGGTGTGGTTCGGCATCATGAATG
                                                                   1150
  Ala Ser Lys Tyr Ala Ser Gln Ser Arg Val Trp Phe Gly Ile Met Asn
                AGCCCCACGACGTGAACATCAACACCTGGGCTGCCACGGTCCAAGAGGTT
                                                                   1200
  Glu Pro His Asp Val Asn Ile Asn Thr Trp Ala Ala Thr Val Gln Glu Val
                GTAACCGCAATCCGCAACGCTGGTGCTACGTCGCAATTCATCTCTTTGCC
                                                                   1250
  Val Thr Ala Ile Arg Asn Ala Gly Ala Thr Ser Gln Phe Ile Ser Leu Pro
                TGGAAATGATTGGCAATCTGCTGGGGCTTTCATATCCGATGGCAGTGCAG
                                                                   1300
  Gly Asn Asp Trp Gln Ser Ala Gly Ala Phe Ile Ser Asp Gly Ser Ala
                CCGCCCTGTCTCAAGTCACGAACCCGGATGGGTCAACAACGAATCTGATT
                                                                   1350
  Ala Ala Leu Ser Gln Val Thr Asn Pro Asp Gly Ser Thr Thr Asn Leu Ile
                TTTGACGTGCACAAATACTTGGACTCAGACAACTCCGGTACTCACGCCGA
                                                                   1400
  Phe Asp Val His Lys Tyr Leu Asp Ser Asp Asn Ser Gly Thr His Ala Glu
                ATGTACTACAAATAACATTGACGGCGCCTTTTCTCCGCTTGCCACTTGGC
                                                                   1450
  Cys Thr Thr Asn Asn Ile Asp Gly Ala Phe Ser Pro Leu Ala Thr Trp
                TCCGACAGAACAATCGCCAGGCTATCCTGACAGAAACCGGTGGTGGCAAC
                                                                   1500
  Leu Arg Gln Asn Asn Arg Gln Ala Ile Leu Thr Glu Thr Gly Gly Gly Asn
                GTTCAGTCCTGCATACAAGACATGTGCCAGCAAATCCAATATCTCAACCA
                                                                   1550
  Val Gln Ser Cys Ile Gln Asp Met Cys Gln Gln Ile Gln Tyr Leu Asn Gln
                GAACTCAGATGTCTATCTTGGCTATGTTGGTTGGGGTGCCGGATCATTTG
                                                                   1600
  Asn Ser Asp Val Tyr Leu Gly Tyr Val Gly Trp Gly Ala Gly Ser Phe
```

FIG. 2B

```
ATAGCACGTATGTCCTGACGGAAACACCGACTAGCAGTGGTAACTCATGG
                                                   1650
Asp Ser Thr Tyr Val Leu Thr Glu Thr Pro Thr Ser Ser Gly Asn Ser Trp
ACGGACACATCCTTGGTCAGCTCGTGTCTCGCAAGAAAGTAGCACTCTGA
                                                   1700
Thr Asp Thr Ser Leu Val Ser Ser Cys Leu Ala Arg Lys  •
GCTGAATGCAGAAGCCTCGCCAACGTTTGTATCTCGCTATCAAACATAGT
                                                   1750
AGCTACTCTATGAGGCTGTCTGTTCTCGATTTCAGCTTTATATAGTTTCA
                                                   1800
TCAAACAGTACATATTCCCTCTGTGGCCACGCAAAAAAAAAAAAAAAA
                                                   1849
```

```
GGGTGGTCTGGATGAAACGTCTTGGCCAAATCGTGATCGATTGATACTCG
                                                    50

CATCTATAAGATGGCACAGATCGACTCTTGATTCACAGACATCCGTCAGC
                                                    100

CCTCAAGCCGTTTGCAAGTCCACAAACACAAGCACAAGCATAGCGTCGCA
                                                    150

ATGAAGTTCCTTCAAGTCCTCCCTGCCCTCATACCGGCCGCCCTGGCCCA
                                                    200
Met Lys Phe Leu Gln Val Leu Pro Ala Leu Ile Pro Ala Ala Leu Ala Gln

AACCAGCTGTGACCAGTGGGCAACCTTCACTGGCAACGGCTACACAGTCA
                                                    250
Thr Ser Cys Asp Gln Trp Ala Thr Phe Thr Gly Asn Gly Tyr Thr Val

GCAACAACCTTTGGGGAGCATCAGCCGGCTCTGGATTTGGCTGCGTGACG
                                                    300
Ser Asn Asn Leu Trp Gly Ala Ser Ala Gly Ser Gly Phe Gly Cys Val Thr

GCGGTATCGCTCAGCGGCGGGGCCTCCTGGCACGCAGACTGGCAGTGGTC
                                                    350
Ala Val Ser Leu Ser Gly Gly Ala Ser Trp His Ala Asp Trp Gln Trp Ser

CGGCGGCCAGAACAACGTCAAGTCGTACCAGAACTCTCAGATTGCCATTC
                                                    400
Gly Gly Gln Asn Asn Val Lys Ser Tyr Gln Asn Ser Gln Ile Ala Ile

CCCAGAAGAGGACCGTCAACAGCATCAGCAGCATGCCCACCACTGCCAGC
                                                    450
Pro Gln Lys Arg Thr Val Asn Ser Ile Ser Ser Met Pro Thr Thr Ala Ser

TGGAGCTACAGCGGGAGCAACATCCGCGCTAATGTTGCGTATGACTTGTT
                                                    500
Trp Ser Tyr Ser Gly Ser Asn Ile Arg Ala Asn Val Ala Tyr Asp Leu Phe

CACCGCAGCCAACCCGAATCATGTCACGTACTCGGGAGACTACGAACTCA
                                                    550
Thr Ala Ala Asn Pro Asn His Val Thr Tyr Ser Gly Asp Tyr Glu Leu

TGATCTGGTAAGCCATAAGAAGTGACCCTCCTTGATAGTTTCGACTAACA
                                                    600
Met Ile Trp
```

FIG. 3A

```
ACATGTCTTGAGGCTTGGCAAATACGGCGATATTGGGCCGATTGGGTCCT
                                                    650
              Leu Gly Lys Tyr Gly Asp Ile Gly Pro Ile Gly Ser

CACAGGGAACAGTCAACGTCGGTGGCCAGAGCTGGACGCTCTACTATGGC
                                                    700
Ser Gln Gly Thr Val Asn Val Gly Gly Gln Ser Trp Thr Leu Tyr Tyr Gly

TACAACGGAGCCATGCAAGTCTATTCCTTTGTGGCCCAGACCAACACTAC
                                                    750
Tyr Asn Gly Ala Met Gln Val Tyr Ser Phe Val Ala Gln Thr Asn Thr Thr

CAACTACAGCGGAGATGTCAAGAACTTCTTCAATTATCTCCGAGACAATA
                                                    800
Asn Tyr Ser Gly Asp Val Lys Asn Phe Phe Asn Tyr Leu Arg Asp Asn

AAGGATACAACGCTGCAGGCCAATATGTTCTTAGTAAGTCACCCTCACTG
                                                    850
Lys Gly Tyr Asn Ala Ala Gly Gln Tyr Val Leu Ser

TGACTGGGCTGAGTTTGTTGCAACGTTTGCTAACAAAACCTTCGTATAGG
                                                    900

CTACCAATTTGGTACCGAGCCCTTCACGGGCAGTGGAACTCTGAACGTCG
                                                    950
Tyr Gln Phe Gly Thr Glu Pro Phe Thr Gly Ser Gly Thr Leu Asn Val

CATCCTGGACCGCATCTATCAACTAAAACCTGGAAACGTGAGATGTGGTG
                                                    1000
Ala Ser Trp Thr Ala Ser Ile Asn  •

GGCATACGTTATTGAGCGAGGGAAAAAAAGCATTGGATCCATTGAAGATG
                                                    1050
```

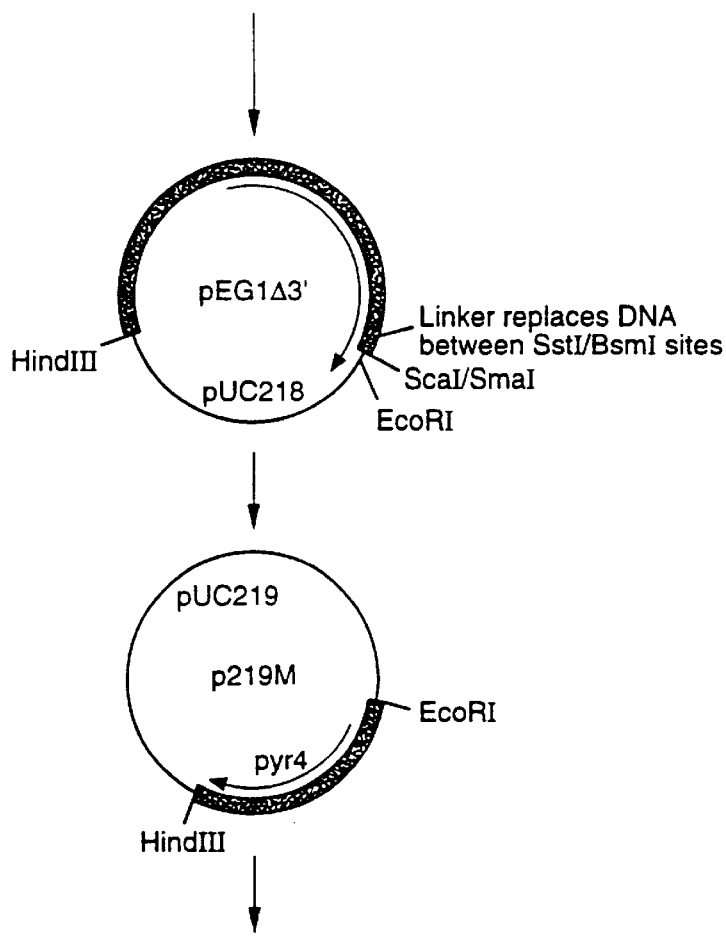
- Digest p219M with EcoRI and HindIII
- Isolate 1.6Kb EcoRI/HindIII *pyr4* gene fragment
- Digest pUC218 with EcoRI SstI and dephosphorylate the ends with calf alkaline phosphotase
- Isolate the HindIII/EcoRI EG1 fragment from pEG1Δ3'
- Ligate together pUC18 EcoRI, EcoRI/HindIII *pyr4* gene fragment and HindIII/EcoRI EG1 fragment
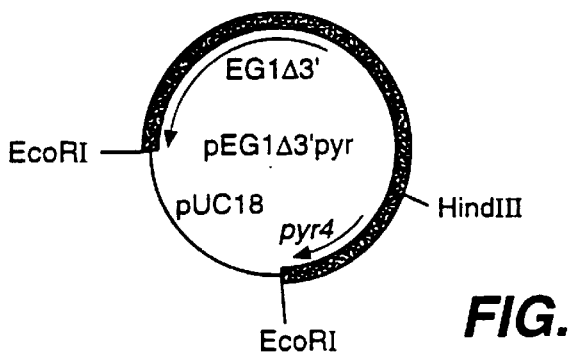
FIG. 4
FIG. 4B

ENZYME FEED ADDITIVE AND ANIMAL FEED INCLUDING IT

This is a continuation of application Ser. No. 08/169,948 filed Dec. 17, 1993, now U.S. Pat. No. 5,861,271.

The present invention relates to an enzyme feed additive and in particular to such an additive which can decrease the feed conversion ratio of a cereal-based feed and/or increase its digestibility.

Improvements in animal feeds to enable animals to digest them more efficiently are constantly being sought. One of the main concerns is to improve the feed conversion ratio (FCR) of a feed without increasing its cost per unit weight. The FCR is the ratio of the amount of feed consumed relative to the weight gain of an animal. A low FCR indicates that a given amount of feed results in a growing animal gaining proportionately more weight. This means that the animal is able to utilise the feed more efficiently. One way in which the FCR of a feed can be improved is to increase its digestibility.

There are various constraints on the digestibility of the nutritional components of a feed such as its starch, fat, protein and amino acid content. These constraints include:

(i) the viscosity of materials present in the animal's gut. Such viscosity is due, at least in part, to soluble non-starch polysaccharides such as mixed-linked β-glucans and arabinoxylans;

(ii) entrapment of nutrients within the cell walls of the feed, particularly those of the aleurone layer in cereals. Such entrapment is caused by the high levels of non-starch polysaccharides in the cell walls of cereals which are relatively resistant to break-down by the animal's digestive system. This prevents the nutrients entrapped within the cells from being nutritionally available to the animal; and (iii) a deficiency in endogenous enzyme activity, both of the animal and of the gut microbial population particularly in a young animal.

The above problems which interfere with digestibility are particularly noticeable in the case of cereal-based diets, and in particular those having a high barley content.

Due to the problem of poor digestibility of nutrients from the feed, it is normally necessary to formulate feeds to contain higher levels of energy providing materials in order to meet the nutritional demands of animals. Such energy providing materials conventionally include starch, fat, sugars, fibre etc. The requirement of including these energy providing materials, or sources of such materials, in a feed adds a considerable extra cost which is disadvantageous from an economic view point.

In an attempt to solve the problem of poor digestibility of cereal-based feeds, it is known to include enzyme supplements such as β-glucanases or xylanases in animal feeds. For example, WO 91/04673 discloses a feed additive for alleviating malabsorption syndrome in poultry which causes reduced digestion. The additive includes a cellulase and a xylanase. JP-A-60-75238 discloses a feed for domestic animals which contains an enzyme cocktail including protease-, cellulase-, amylase- and lipase-activities. This reference speculates that these various enzyme activities enable fermentation microbes to grow and that these become useful nutritional components of the feed.

Whole cellulase is a mixture of different enzymes which cooperate to hydrolyze cellulose (β-1,4-D-glucan linkages) and/or derivatives thereof (e.g. phosphoric acid swollen cellulose) and give as primary products compounds such as glucose, cellobiose, and cellooligo-saccharides. Whole cellulase is made up of several different enzyme classifications including enzymes having exo-cellobiohydrolase activity, endoglucanase activity and β-glucosidase activity.

For example, the whole cellulase produced by the fungus *Trichoderma longibrachiatum* comprises two exo-cellobiohydrolases, CBHI and CBHII, at least three endoglucanases, EGI, EGII and EGIII, and at least one β-glucosidase. A representative fermentation from *T. longibrachiatum* may produce a whole cellulase including by protein weight 45–55% CBHI, 13–15% CBHII, 11–13% EGI, 8–10% EGII, 1–4% EGIII and 0.5–1% BG. However, it should be noted that actual concentrations of a specific cellulase component will vary according to numerous factors, including fermentation conditions, substrate concentrations and strain type. Thus, in a representative fermentation, *Trichoderma longibrachiatum* produces a whole cellulase having from 58–70% of cellobiohydrolases.

Each endoglucanase of *T. longibrachiatum* has its own distinct characteristics. Thus, EGI in addition to cellulase activity is known to hydrolyze xylan. EGII and EGIII by comparison do not show significant xylanase activity, at least according to azo-xylan native PAGE overlay. Further, it is known that EGI, EGII and EGV contain structurally distinct cellulose binding domains (CBD's). On the other hand, EGIII does not appear to contain a structurally distinct binding domain and has been shown to have a lower affinity for crystalline cellulose compared to EGI or EGII.

WO 92/06209 discloses processes for transforming the filamentous fungus *Trichoderma reesei* (now called "*T. longibrachiatum*") which involves the steps of treating a *T. reesei* strain with substantially homologous linear recombinant DNA to permit homologous transformation and then selecting the resulting *T. reesei* transformants. For instance, transformants are described in which certain targeted genes are deleted or disrupted within the genome and extra copies of certain native genes such as those encoding EGI and EGII are homologously recombined into the strain. It is noted in this reference that cellulase compositions obtained from strains deficient in CBHI and CEHII components are useful as components of a detergent cleaning composition. Such cellulase compositions are of course relatively enriched When used in vivo, endoglucanases and cellobiohydrolases are considered to act synergistically in the hydrolysis of cellulose to small cello-oligosaccharides (mainly cellobiose), which are subsequently hydrolysed to glucose by the action of β-glucosidase. In addition to hydrolyzing the β-1,4 linkages in cellulose, endo-1,4-β-glucanase (EC 3.2.1.4) will also hydrolyze 1,4 linkages in β-glucans also containing 1,3-linkages. The endoglucanases act on internal linkages to produce cellobiose, glucose and cello-oligosaccharides. The cellobiohydrolases act on the chain ends of cellulose polymers to produce cellobiose as the principal product.

Whole cellulase obtained from *T. longibrachiatum* has been used in combination with barley in fields such as brewing and in animal nutrition for several years. One of the benefits of adding cellulases to barley-based diets for livestock is to increase the digestibility of various components present in the diet including protein and amino acids. As a result, dietary input costs can be reduced without loss of performance, and excretion of nitrogen in the manure can be significantly reduced. This reduces the environmental impact of intensive livestock farming.

Endosperm cell walls of barley contain a high proportion of high molecular weight, water-soluble mixed-linked β-(1, 3)(1,4)-glucans. When solubilised, these poly-saccharides cause an increase in the solution's viscosity. For example, if barley is fed to broiler chickens, this leads to a relatively high level of viscosity in the region of their gastrointestinal tract, which results in reduced efficiency of digestion and growth depression.

Organisms which produce or express cellulose enzyme complexes often also express xylanase activity. For example, two different xylanase enzymes produced by *T. longibrachiatum* have been identified. The purification of these two different xylanases, one referred to as high pI xylanase (having a pI of about 9.0) and the other referred to as low pI xylanase (having a pI of about 5.2), as well as the cloning and sequencing of the gene for each xylanase is described in detail in WO 92/06209 and WO 93/24621. FIG. 16 of this document sets out the deduced amino acid sequences for both the low pI and high pI gene products. Example 22 also teaches how to create *T. longibrachiatum* strains which over-express the low pI and high pI xylanase genes.

As mentioned above, the use of cellulases as an additive to animal feeds is known in the art. Such cellulases of course possess a natural balance between their cellobiohydrolase and endoglucanase contents. AB also mentioned above, in naturally occurring strains of *T. longibrachiatum,* the CBHs may comprise 58–70% by weight of the cellulase proteins.

The present invention is based upon a study to identify which components of the cellulose proteins are able to improve the nutritional benefits of cereal-based feeds such as those including barley. Specific attention has been paid to the effects of the individual enzymes constituting whole cellulase, and in particular the endoglucanases, on viscosity reduction of soluble mixed-linked β-(1,3) (1,4)-glucans of barley. This is because this is known to be one of the primary modes of action of whole cellulose. The present invention has been made as a result of this research to identify those specific components of the cellulose enzyme system, and their relative amounts, which advantageously improve the feed conversion ratio (FCR) of a cereal-based feed and/or increase its digestibility.

In the description and claims which follow, the following are definitions of some of the technical terms which are employed.

"Fungal cellulase" means an enzyme composition derived from fungal sources or microorganisms genetically modified so as to incorporate and express all or part of the cellulase genes obtained from a fungal source.

The term "Trichoderma" refers to any fungal strain which is or has previously been classified as Trichoderma or which is currently classified as Trichoderma. Such species include *Trichoderma longibrachiatum, Trichoderma reesei* and *Trichoderma viride.*

The term "EG" refers to any endoglucanase, for example EGI, EGII, EGIII or EGV produced by *T. longibrachiatum,* or any derivative of any such endoglucanase which possesses endoglucanase activity.

An EG "derivative" includes for example, EGI, EGII, EGIII and EGV from Trichoderma in which there is an addition of one or more amino acids to either or both of the C- and N-terminal ends of the EG, a substitution of one or more amino acids at one or more sites throughout the EG, a deletion of one or more amino acids within or at either or both ends of the EG, or an insertion of one or more amino acids at one or more sites in the EG such that endoglucanase activity is retained in the derivatized EG. The term EG "derivative" also includes the core domains of the endoglucanase enzymes that have attached thereto one or more amino acids from the linker regions.

The term "truncated cellulase", as used herein, refers to a protein comprising a truncated cellulase core of exo-cellobiohydrolase or endoglucanase, for example, EGI, EGII, EGV, CBHI and CBHII, or derivatives of either. EGV is described in Molecular Microbiology, Vol. 13, No. 2 (1994) at pages 219–228. As stated above, many cellulase enzymes, such as EGI, EGII and EGV, are believed to be bifunctional in that they contain regions or domains which are directed toward both catalytic or hydrolytic activity with respect to the cellulose substrate, and also non-catalytic cellulose binding activity. Thus, a truncated cellulase is a cellulase which lacks binding domain cellulose binding activity.

It is believed that the catalytic core and the cellulose binding domain of a cellulose enzyme act together in a synergistic manner to effect efficient hydrolysis of cellulose fibers in a cellulose containing feed. It is further believed that cellulase catalytic activity and cellulose binding activity may be identified as being specific to distinct structural regions, or may be present in the same structural region. For example, as indicated above, many cellulose enzymes, including several of those from *T. longibrachiatum* are known to incorporate a catalytic core domain subunit which is attached via a linker region to a cellulose binding domain subunit. However, other cellulase enzymes are believed to have a catalytic core domain which is structurally integral to a cellulose binding domain, e.g., the two regions are not separated by a linker and do not represent distinct structural entities. In such a cellulase enzyme, it is believed that a specific peptide or group of related amino acid residues may be responsible for cellulose binding activity. Accordingly, it is within the scope of the present invention that such a binding domain would be altered so as to reduce the cellulose binding activity of the cellulase by, for example, genetic engineering or chemical modification.

A "truncated cellulase derivative" encompasses a truncated cellulase core, as defined herein, wherein there may be an addition or deletion of one or more amino acids to either or both of the C- and N-terminal ends of the truncated cellulose, or a substitution, insertion or deletion of one or more amino acids at one or more sites throughout the truncated cellulase. Derivatives are interpreted to include mutants that preserve their character as truncated cellulase core, as defined below. It is also intended that the term "derivative of a truncated cellulase" includes core domains of the exoglucanase or endoglucanase enzymes that have attached thereto one or more amino acids from the linker regions.

A truncated cellulase derivative further refers to a protein substantially similar in structure and biological activity to a truncated cellulose core domain protein, but which has been genetically engineered to contain a modified amino acid sequence. Thus, provided that the two proteins possess a similar activity, they are considered "derivatives" as that term is used herein even if the primary structure of one protein does not possess the identical amino acid sequence to that found in the other.

It is contemplated that a truncated cellulase derivative may be derived from a DNA fragment encoding a truncated catalytic core domain which further contains an addition of one or more nucleotides internally or at the 5' or 3' end of the DNA fragment, a deletion of one or more nucleotides internally or at the 5' or 3' and of the DNA fragment or a substitution of one or more nucleotides internally or at the 5' or 3' end of the DNA fragment wherein the functional activity of the catalytic core domain ( truncated cellulase derivative) is retained. Such a DNA fragment ("variant DNA fragment") comprising a cellulase catalytic core may further include a linker or hinge DNA sequence or portion thereof which is attached to the core or binding domain DNA sequence at either the 5' or 3' end wherein the functional activity of the encoded truncated cellulase core domain (truncated cellulase derivative) is retained.

The term "truncated cellulase core" or "truncated cellulase region" refers herein to a peptide comprising the catalytic core domain or region of exo-cellobiohydrolase or endoglucanase, for example, EGI, EGII or EGIII or a derivative thereof that is capable of enzymatically cleaving cellulose polymers, including but not limited to pulp or phosphoric acid swollen cellulose. However, a truncated cellulase core will not possess cellulose binding activity attributable to a cellulose binding domain or region. A truncated cellulase core is distinguished from a non-truncated cellulase which, in an intact form, possesses no cellulose binding domain or region. A truncated cellulase core may include other entities which do not include cellulose binding activity attributable to cellulose binding domain or region. For example, the presence of a linker or hinge is specifically contemplated. Similarly the covalent attachment of another enzymatic entity to the truncated cellulase core is also specifically contemplated.

The performance (or activity) of a protein containing a truncated catalytic core or a derivative thereof may be determined by methods well known in the art. (See Wood, T. M. et al. in Methods in Enzymology, Vol. 160, Editors: Wood, W. A. and Kellogg, S. T., Academic Press, pp. 87–116, 1988). For example, such activities can be determined by hydrolysis of phosphoric acid-swollen cellulose and/or soluble oligosaccharides followed by quantification of the reducing sugars released. In this case the soluble sugar products, released by the action of cellobiohydrolase or endoglucanase cellulase core domains or derivatives thereof, can be detected by HPLC analysis or by use of calorimetric assays for measuring reducing sugars. It is expected that these catalytic domains or derivatives thereof will retain at least 10% of the activity exhibited by the intact enzyme when each is assayed under similar conditions and dosed based on similar amounts of catalytic domain protein.

The term "cellulose binding domain" refers herein to an amino acid sequence of the endoglucanase comprising the binding domain of an endoglucanase, for example, EGI or EGII, that non-covalently binds to a polysaccharide such as cellulose. It is believed that cellulose binding domains (CBDs) function independently from the catalytic core of the endoglucanase enzyme to attach the protein to cellulose. Truncated endoglucanases used in this invention lack the CBD but include at least the core or catalytic domain.

The term "linker region" or "hinge region" refers to the short peptide region that links together the two distinct functional domains of the fungal endoglucanases, i.e., the core domain and the binding domain. These domains in *T. longibrachiatum* cellulases are linked by a peptide rich in Ser, Thr and Pro.

A "signal sequence" refers to any sequence of amino acids bound to the N-terminal portion of a protein which facilitates the secretion of the mature form of the protein outside of the cell. This definition of a signal sequence is a functional one. The mature form of the extracellular protein lacks the signal sequence which is cleaved off during the secretion process.

The term "host cell" means both the cells and protoplasts created from the cells of Trichoderma.

The term "DNA construct or vector" (used interchangeably herein) refers to a vector which comprises one or more DNA fragments or DNA variant fragments encoding any one of the truncated endoglucanases or derivatives described above.

The term "functionally attached to" means that a regulatory region, such as a promoter, terminator, secretion signal or enhancer region is attached to a structural gene and controls the expression of that gene.

The term "whole cellulase" means the complete cellulase system as produced by a naturally occurring microorganism.

Based upon the above considerations, it is an object of the present invention to provide enzyme-based feed additives which improve the FCR and/or increase the digestibility of a cereal-based feed.

According to one aspect, the present invention provides the use of a composition as a feed additive which comprises one or more endoglucanases, and 0–20% by weight, based upon the content of cellulase proteins in the composition, of a cellobiohydrolase.

As mentioned above, whole cellulase from *T. longibrachiatum* (i.e. strains occurring naturally) typically contains 58–70% by weight of cellobiohydrolases or more based on the total weight of enzymes having cellulase activity. The composition for use as a feed additive provided by the present invention may be obtained by enriching the content of endoglucanases produced by a suitable microorganism through purification, addition of purified endoglucanase or by adding additional genes to overproduce endoglucanase. In addition, or alternatively, the relative content of cellobiohydrolases produced by the microorganism may be decreased compared to whole cellulase through purification procedures or by modifying or deleting those genes which encode cellobiohydrolase. It is particularly preferred that the feed additive should be free of cellobiohydrolases, so that their content in the additive is 0% by weight.

In a second aspect, the present invention provides an enzyme-based feed additive which comprises at least one of EGIII, EGI which lacks the cellulose binding domain and EGII which lacks the cellulose binding domain, and 0–20% by weight based upon the content of cellulase proteins in the additive, of a cellobiohydrolase.

The production of such structurally modified endoglucanases by genetic engineering techniques is described in detail below.

In a third aspect, the present invention provides an enzyme-based feed additive comprising a cereal-based carrier, one or more endoglucanases, and 0–20% by weight, based upon the content of cellulase proteins in the additive, of a cellobiohydrolase. In such an additive, the cereal-based carrier may be milled wheat, maize or milled soya. Further, the carrier may be a by-product of any of these materials.

Endoglucanases suitable for use in the present invention include those derived from bacterial sources, for example, Bacillus sp., including *Bacillus subtilis*, Strepromyces sp., Clostridium sp., including *Clostridium thermocellum* and *Clostridium cellulovorans*. Alternatively, fungal sources of cellulase are suitable. Suitable fungal sources include Trichoderma sp., *Trichoderma longibrachiatum, Trichoderma viride, Trichoderma koningii,* Myceliophthora sp., Phanerochaete sp., Schizophyllum sp., Penicillium sp., Aspergillus sp., Geotricum sp., Fusarium sp., *Fusarium oxysporum,* Humicola sp., *Humicola insolens,* and Mucor sp., including *Mucor miehei.*

Endoglucanase type components may not include components traditionally classified as endoglucanases using activity tests such as the ability of the component (a) to hydrolyze soluble cellulose derivatives such as carboxymethylcellulose (CMC), thereby reducing the viscosity of CMC containing solutions, (b) to readily hydrolyze hydrated forms of cellulose such as phosphoric acid, swollen cellulose (e.g., Walseth cellulose) and hydrolyze less readily the more highly crystalline forms of cellulose (e.g., Avicel, Solkafloc, etc.). On the other hand, it is believed that not all endoglucanase components, as defined by such activity tests, will enhance the nutritional value of feeds. Accordingly, it is more accurate for the purposes herein to define endoglucanase type components as those enzymes which possess feed nutritional enhancement properties comparable to those possessed by the endoglucanase components of *Trichoderma longibrachiatum*.

Fungal cellulases can contain more than one endoglucanase type component. The different components generally have different isoelectric points, different molecular weights, different degrees of glycosylation, different substrate specificities, different enzymatic action patterns, etc. The different isoelectric points of the components allow for their separation via ion exchange chromatography and the like. In fact, the isolation of components from different sources is known in the art. See, for example Bjork et al., U.S. Pat. No. 5,120,463; Schulein et al., International Application WO 89/09259; Wood et al., Biochemistry and Genetics of Cellulose Degradation, pp. 31–52 (1988); Wood et al., Carbohydrate Research, Vol. 190, pp. 279–297 (1989); and Schulein, Methods in Enzymology, Vol. 160, pp. 234–242 (1988). The entire disclosure of each of these references is incorpoated herein by reference.

The term "EGI cellulase" refers to the endoglucanase component derived from *Trichoderma spp.* characterized by a pH optimum of about 4.0 to 6.0, an isoelectric point (pI) of from about 4.5 to 4.7, and a molecular weight of about 47 to 49 Kdaltons. Preferably, EGI cellulase is derived from either *Trichoderma longibrachiatum* or from *Trichoderma viride*. EGI cellulase derived from *Trichoderma longibrachiatum* has a pH optimum of about 5.0, an isoelectric point (pI) of about 4.7 and a molecular weight of about 47 to 49 Kdaltons. EGI cellulase derived from *Trichoderma viride* has a pH optimum of about 5.0, an isoelectric point (pI) of about 5.3 and a molecular weight of about 50 Kdaltons.

It is noted that EGII has previously been referred to as "EGIII" by some authors but current nomenclature uses the term EGII. In any event the EGII protein differs substantially from the EGIII protein in its molecular weight, pI and pH optimum. The term "EGII cellulase" refers to the endoglucanase component derived from Trichoderma spp. characterized by a pH optimum of about 4.0 to 6.0, an isoelectric point (pI) of about 5.5, and a molecular weight of about 35 Kdaltons. Preferably, EGII cellulase is derived from either *Trichoderma longibrachiatum* or from *Trichoderma viride*.

The term "EGIII cellulase" refers to the endoglucanase component derived from Trichoderma spp. characterized by a pH optimum of about 5.0 to 7.0, an isoelectric point (pI) of from about 7.2 to 8.0, and a molecular weight of about 23 to 28 Kdaltons. Preferably, EGIII cellulase is derived from either *Trichoderma longibrachiatum* or from *Trichoderma viride*. EGIII cellulase derived from *Trichoderma longibrachiatum* has a pH optimum of about 5.5 to 6.0, an isoelectric point (pI) of about 7.4 and a molecular weight of about 25 to 28 Kdaltons. EGIII cellulase derived from *Trichoderma viride* has a pH optimum of about 5.5, an isoelectric point (pI) of about 7.7, and a molecular weight of about 23.5 Kdaltons.

"Exo-cellobiohydrolase type components" ("CBH type components") refers to all those cellulase components which exhibit similar feed activity properties to CBHI and CBHII of *Trichoderma longibrachiatum*. In this regard, when used in combination with EG type components, CBHI and CBHII type components (as defined above) reduce the effectiveness of a cellulase supplement for animal feed in terms of the feed conversion ratio and/or feed digestibility.

Such exo-cellobiohydrolase type components may not include components traditionally classed as exo-cellobiohydrolases using activity tests such as those used to characterize CBHI and CBHII from *Trichoderma longibrachiatum*. For example, such components (a) are competitively inhibited by cellobiose (K; approximately 1 mM); (b) are unable to hydrolyze to any significant degree substituted celluloses, such as carboxymethylcellulose, etc., and (c) hydrolyze phosphoric acid swollen cellulose and to a lesser degree highly crystalline cellulose. On the other hand, it is believed that some cellulase components which are characterized as CBH components by such activity tests, will enhance the nutritional value of feeds. Accordingly, it is believed to be more accurate for the purposes herein to define such exo-cellobiohydrolases as EG type components because these components possess similar functional properties in animal uses comparable to those of the endoglucanase components of *Trichoderma longibrachiatum*.

"β-glucosidase (BG) components" refer to those components of cellulase which exhibit BG activity; that is to say that such components will act from the non-reducing end of cellobiose and other soluble cellooligosaccharides ("cellobiose") and give glucose as the sole product. BG components do not adsorb onto or react with cellulose polymers. Furthermore, such BG components are competitvely inhibited by glucose ($K_i$ approximately 1 mM). While in a strict sense, BG components are not literally cellulases because they cannot degrade cellulose, such BG components are included within the definition of the cellulase system because these enzymes facilitate the overall degradation of cellulose by further degrading the inhibitory cellulose degradation products (particularly cellobiose) produced by the combined action of CBH components and EG components. Without the presence of BG components, moderate or little hydrolysis of crystalline cellulose will occur. BG components are often characterized by using aryl substrates such as p-nitrophenol-β-D-glucoside (PNPG) and thus are often called aryl-glucosidases. It should be noted that not all aryl-glucosidases are BG components, in that some do not hydrolyze cellobiose.

It is contemplated that the presence or absence of BG components in the cellulase composition can be used to regulate the activity of any CBH components in the composition. Specifically, because cellobiose is produced during cellulose degradation by CBH components, and because high concentrations of cellobiose are known to inhibit CBH activity, and further because such cellobiose is hydrolyzed to glucose by BG components, the absence of BG components in the cellulase composition will "turn-off" CBH activity when the concentration of cellobiose reaches inhibitory levels. It is also contemplated that one or more additives (e.g., cellobiose, glucose, etc.) can be added to the cellulase composition to effectively "turn-off", directly or indirectly, some or all of the CBHI type activity as well as other CBH activity. When such additives are employed, the resulting composition is considered to be a composition suitable for use in this invention if the amount of additive is sufficient to lower the CBH type activity to levels equal to or less than the CBH type activity levels achieved by using the cellulase compositions described herein.

On the other hand, a cellulase composition containing added amounts of BG components may increase overall hydrolysis of cellulose if the level of cellobiose generated by the CBH components becomes restrictive of such overall hydrolysis in the absence of added BG components.

Methods to either increase or decrease the amount of BG components in the cellulase composition are disclosed in U.S. Ser. No. 07/807,028 filed Dec. 10, 1991 which is a continuation-in-part of U.S. Ser. No. 07/625,140, filed Dec. 10, 1990 (corresponding to EP-A-0 562 003), all of which are incorporated herein by reference in their entirety.

Fungal cellulases can contain more than one BG component. The different components generally have different isoelectric points which allow for their separation via ion exchange chromatography and the like. Either a single BG component or a combination of BG components can be employed.

In a preferred embodiment, the endoglucanase components suitable for use in the present invention are those which exhibit properties similar to those obtainable from *Trichoderma longibrachiatum*, i.e., EGI, EGII and EGIII. Thus, the term "EG type components" refers to all of those cellulase components or combination of components which confer improved properties to feed in a manner similar to the endoglucanase components of *Trichoderma longibrachiatum*. In this regard, the endoglucanase components of *Trichoderma longibrachiatum* (specifically, EGI, EGII, EGIII and the like, either alone or in combination) impart characteristics such as improved feed conversion ratio, reduced gut viscosity and improved animal weight gain to animals fed grains treated with them as compared to untreated feed, or feed treated with whole cellulase. Methods for the preparation of EGI, EGII and EGIII are described in detail in WO 92/06209.

It is possible that components other than CBH type components present in the whole cellulase composition may cause undesirable gut viscosity, feed conversion ratio increase and lessened animal weight gain. Therefore, it is contemplated that the use of enriched endoglucanases, such as EGI, EGII or EGIII, may eliminate some or all of the problems which occur when whole cellulase is used.

It has been found that the inclusion of an endoglucanse enriched feed additive in a cereal-based diet of an animal enables the animal to digest the diet more efficiently. This is particularly the case in cereal-based feeds including barley where the presence of the above feed additive improves the feed conversion ratio and/or increases the digestibility of the cereal-based feed. Cereal-based feeds usually include at least 25% by weight of cereal and preferably at least 35% by weight. In addition to or instead of barley, the cereal may include one or more of wheat, triticale, rye and maize.

The endoglucanase enriched feed additives provided by the present invention also enable a conventional cereal-based feed to be modified by reducing its energy, and/or protein, and/or amino acid content whilst simultaneously maintaining the same nutritional levels of energy, protein, and amino acids available to the animal. This means that the amounts of costly energy and protein supplements conventionally included in an animal feed can be reduced as compared to conventional feeds. Energy supplements include fat. Protein supplements include fish-meal, wheat-meal, soya-bean, rapeseed, or canola. This results in a significant reduction in the cost per unit weight of the animal feed without decreasing its nutritional value. Alternatively, or even additionally, the amounts of amino acid supplements can be reduced as compared to conventional feeds which can also result in significant cost savings.

The enzyme feed additive according to the present invention can be prepared in a number of ways. For instance, it can be prepared simply by mixing different enzymes having the appropriate activities to produce an enzyme mix. This enzyme mix can be either mixed directly with a feed, or more conventionally impregnated onto a cereal-based carrier material such as milled wheat, maize or soya flour. A by-product of any of these products may also be used. Such an impregnated carrier constitutes an enzyme feed additive in accordance with the third aspect of the present invention.

As an alternative, a cereal-based carrier formed from e.g. milled wheat or maize can be impregnated either simultaneously or sequentially with enzymes having the appropriate activities. For example, a milled wheat carrier may be sprayed with the one or more endoglucanases. Other enzymes may also be incorporated as appropriate. The carrier material impregnated with these enzymes also constitutes an enzyme feed additive in accordance with the third aspect of the present invention.

The feed additive provided by the present invention may be mixed directly with the animal feed, such as one comprising barley, to prepare the final feed. Alternatively, the feed additive may be mixed with one or more other feed additives such as a vitamin feed additive, a mineral feed additive and an amino acid feed additive. The resulting feed additive including several different types of components can then be mixed in an appropriate amount with the feed.

The resulting cereal-based feed preferably comprises 0.000001–0.1 g/kg of total endoglucanases, more preferably 0.00001–0.01 g/kg and most preferably 0.0001–0.001 g/kg.

The endoglucanases for use in the feed additive of the present invention can be obtained by growing a fungus such as a naturally occurring strain of Trichoderma. Thus, the fungus can be cultivated, after which it is removed from the broth. The cellulase enzyme complex can then be isolated from the broth and separated into its individual components from which the endoglucanases are in turn isolated. This technique is however not so preferred because of the purification steps necessary.

A more preferred method of preparing the enzyme feed additive of the present invention is to construct by genetic manipulation a host microorganism, such as the fungus Trichoderma, which produces the desired enzymes in the appropriate relative amounts. This can be done for instance by increasing the copy number of the gene encoding endoglucanases (e.g. EGI, EGII and/or EGIII) and/or by using a suitably strong promoter in front of any of the above endoglucanase genes. Alternatively or additionally the host strain can be deleted for certain cellulase genes (e.g. those encoding CBHI and/or CBHII). Such procedures are fully explained in the disclosure of WO 92/06209 in the case of transforming *T. reesei*.

The enzyme feed additive provided by the present invention may also include other enzymes such as xylanase, protease, α-amylase, glucoamylase, lipase, pectinase, mannanase, α-galactosidase, α-arabinofuranosidase or phytase. Enzymes having the desired activities may for instance be mixed with the endoglucanases used in the present invention either before impregnating these on a cereal-based carrier or alternatively such enzymes may be impregnated simultaneously or sequentially on such a cereal-based carrier. The carrier is then in turn mixed with a cereal-based feed to prepare the final feed. It is also possible to formulate the enzyme feed additive as a solution of the individual enzyme activities and then mix this solution with a feed material pre-formed as pellets or as a mash.

It is also possible to include the enzyme feed additive in the animals' diet by incorporating it into a second (and different) feed or drinking water which the animal also has access to. Accordingly, it is not essential that the enzyme mix provided by the present invention is incorporated into the cereal-based food itself, although such incorporation forms a particularly preferred aspect of the present invention.

In one preferred embodiment, the xylanase added as an additional enzyme is the high pI xylanase and/or the low pI xylanase obtainable from *T. longibrachiatum* obtainable by the method of Example 22 of WO 92/06209. It is particularly preferred that the xylanase is the high pI xylanase.

According to a further preferred embodiment, the protease added as an additional enzyme is a subtilisin or mutant thereof derived from the genus Bacillus. Suitable strains of Bacillus include but are not limited to *B. amyloliquefaciens, B. lentus, B. licheniformis, B. subtilis,* or *B. alcalophilus.*

The subtilisin may also be a mutant subtilisin having an amino acid sequence not found in nature but which is derived from a precursor subtilisin by inserting, deleting or replacing one or more different amino acid residues in the precursor subtilisin. Suitable mutant subtilisins are described in EP-A-0 130 756 corresponding to U.S. Pat. No. Re-34686 (including mutations at positions +155, +104, +222, +166, +133, +169, +189, +217, +156, +152); EP-A-0 251 446; WO 91/06637 etc. The most preferred subtilisin is a mutant subtilisin which comprises a substitution at the amino acid residue position equivalent to tyr+217 of *B. amyloliquefaciens* subtilisin with leucine.

Methods of producing such mutant subtilisins are described in detail in the publications U.S. Pat. No. Re-34606 and EP-A-0 251 446.

The cereal-based animal feeds including the additive of the present invention are suitable for animals such as pigs, ruminants such as sheep and cows, and poultry such as chickens, turkeys, geese and ducks. The feeds though are particularly suitable for poultry and pigs, and in particular broiler chickens.

As previously mentioned, the enzyme feed additive according to the present invention is preferably obtained by growing a genetically modified strain of the fungus Trichoderma. This is because of its well known capacity to secrete whole cellulases in large quantities. This modified strain may be derived from *T. longibrachiatum, T. reesei* or *T. viride.* The genome of such strains can be modified to over-express or delete one or more of the enzyme components making up whole cellulase.

Microorganism cultures are grown to a stationary phase, filtered to remove the cells and the remaining supernatant is concentrated by ultrafiltration to obtain the endoglucanase or derivative thereof.

In a particular aspect of the above method, the medium used to cultivate the transformed host cells may be any medium suitable for endoglucanase production in Trichoderma. The endoglucanase or derivative thereof is recovered from the medium by conventional techniques including separation of the cells from the medium by centrifugation, or filtration, precipitation of the proteins in the supernatant or filtrate with salt, for example, ammonium sulphate, followed by chromatography procedures such as ion exchange chromatography, affinity chromatography and the like.

Alternatively, the final protein product may be isolated and purified by binding to a polysaccharide substrate or antibody matrix. The antibodies (polyclonal or monoclonal) may be raised against endoglucanase core domain peptides, or synthetic peptides may be prepared from portions of the core domain and used to raise polyclonal antibodies.

It is further contemplated by the present invention that the DNA fragment or variant DNA fragment encoding the endoglucanase or derivative may be functionally attached to a fungal promoter sequence, for example, the promoter of the cbh1 or egl1 gene. Also contemplated by the present invention is manipulation of the Trichoderma strain via transformation such that a DNA fragment encoding an endoglucanase or derivative thereof is inserted within the genome. It is also contemplated that more than one copy of an endoglucanase DNA fragment or DNA variant fragment may be recombined into the strain.

A selectable marker must first be chosen so as to enable detection of the transformed fungus. Any selectable marker gene which is expressed in Trichoderma can be used in the present invention so that its presence in the transformants will not materially affect the properties thereof. The selectable marker can be a gene which encodes an assayable product. The selectable marker may be a functional copy of a Trichoderma gene which if lacking in the host strain results in the host strain displaying an auxotrophic phenotype.

The host strains used could be derivatives of Trichoderma which lack or have a non-functional gene or genes corresponding to the selectable marker chosen. For example, if the selectable marker of pyr4 is chosen, then a specific pyr derivative strain is used as a recipient in the transformation procedure. Other examples of selectable markers that can be used in the present invention include the Trichoderma genes equivalent to the *Aspergillus nidulans* genes argb, trpc, niaD and the like.

The corresponding recipient strain must therefore be a derivative strain such as $argB^-$, $trpC^-$, $niaD^-$, and the like.

The strain is derived from a starting host strain which is any Trichoderma strain. However, it is preferable to use a *T. longibrachiatum* cellulase over-producing strain such as RL-P37, described by Sheir-Neiss et al. in Appl. Microbiol. Biotechnology, 20 (1984) pp. 46–53, since this strain secretes elevated amounts of cellulase enzymes. This strain is then used to produce the derivative strains used in the transformation process.

The derivative strain of Trichoderma can be prepared by a number of techniques known in the art. An example is the production of $pyr4^-$ derivative strains by subjecting the strains to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select $pyr4^-$ derivative strains which lack a functional orotidine monophosphate decarboxylase enzyme and require uridine for growth by selecting for FOA resistance. Using the FOA selection technique, it is also possible to obtain uridine requiring strains which lack a functional orotate pyrophosphoribosyl transferase. It is possible to transform these cells with a functional copy of the gene encoding this enzyme (Berges and Barreau, 1991, Curr. Genet. 19 pp359–365). Since it is easy to select derivative strains using the FOA resistance technique in the present invention, it is preferable to use the pyr4 gene as a selectable marker.

In a preferred embodiment of the present invention, Trichoderma host cell strains are deleted of one or more cellobiohydrolase genes prior to introduction of a DNA construct or plasmid containing the DNA fragment encoding the endoglucanase of interest. It is preferable to express an endoglucanase, derivative thereof or covalently linked endoglucanase domain derivative in a host that is missing one or more cellobiohydrolase genes in order to simplify the identification and subsequent purification procedures. Any gene from Trichoderma which has been cloned can be deleted such as cbh1 or cbh2.

The desired gene that is to be deleted from the transformant is inserted into a plasmid by methods known in the art. This plasmid is selected such that unique restriction enzyme sites are present therein to enable the fragment of Trichoderma DNA to be subsequently removed as a single linear piece. The plasmid containing the gene to be deleted or disrupted is then cut at appropriate restriction enzyme site (s), internal to the coding region, the gene coding sequence or part thereof may be removed therefrom and the selectable marker (e.g. pry 4) inserted. Flanking DNA sequences from the locus of the gene to be deleted or disrupted, preferably between about 0.5 to 2.0 kb, remain on either side of the selectable marker gene.

A single DNA fragment containing the deletion construct is then isolated from the plasmid and used to transform the appropriate pyr⁻ Trichoderma host. Transformants are selected based on their ability to express the pyr4 gene product and thus complement the uridine auxotrophy of the host strain. Southern blot analysis is then carried out on the resultant transformants to identify and confirm a double cross-over integration event which replaces part or all of the coding region of the gene to be deleted with the pyr4 selectable markers.

Although specific plasmid vectors are described above, the present invention is not limited to the production of these vectors. Various genes can be deleted and replaced in the Trichoderma strain using the above techniques. Any available selectable markers can be used, as discussed above. Potentially any Trichoderma gene which has been cloned, and thus identified, can be deleted from the genome using the above-described strategy.

The expression vector of the present invention carrying the inserted DNA fragment or variant DNA fragment encoding the endoglucanase or derivative thereof of the present invention may be any vector which is capable of replicating autonomously in a given host organism, typically a plasmid. In preferred embodiments two types of expression vectors for obtaining expression of genes or truncations thereof are contemplated. The first contains DNA sequences in which the promoter, gene coding region, and terminator sequence all originate from the gene to be expressed. Gene truncation if required is obtained by deleting away the undesired DNA sequences (coding for unwanted domains) to leave the domain to be expressed under control of its own transcriptional and translational regulatory sequences. A selectable marker is also contained on the vector allowing the selection for integration into the host of multiple copies of the novel gene sequences.

For example, a DNA construct which can be termed pEGID3'pyr contains the EGI cellulase core domain under the control of the EGI promoter, terminator, and signal sequences. The 3' end on the EGI coding region containing the cellulose binding domain has been deleted. The plasmid also contains the pyr4 gene for the purpose of selection.

The second type of expression vector is preassembled and contains sequences required for high level transcription and a selectable marker. It is contemplated that the coding region for a gene or part thereof can be inserted into this general purpose expression vector such that it is under the transcriptional control of the expression cassette's promoter and terminator sequences.

For example, pTEX is such a general purpose expression vector. Genes or part thereof can be inserted downstream of the strong CBHI promoter.

In the vector, the DNA sequence encoding the endoglucanase should be operably linked to transcriptional and translational sequences, i.e., a suitable promoter sequence and signal sequence in reading frame to the structural gene. The promoter may be any DNA sequence which shows transcriptional activity in the host cell and may be derived from genes encoding proteins either homologous or heterologous to the host cell. The signal peptide provides for extracellular expression of the endoglucanase or derivatives thereof. The DNA signal sequence is preferably the signal sequence naturally associated with the truncated gene to be expressed, however the signal sequence from any endoglucanase is contemplated in the present invention.

The procedures used to ligate the DNA sequences coding for the truncated endoglucanases or derivatives thereof with the promoter, and insertion into suitable vectors containing the necessary information for replication in the host cell are well known in the art.

The DNA vector or construct described above may be introduced in the host cell in accordance with known techniques such as transformation, transfection, microinjection, microporation, biolistic bombardment and the like.

In a preferred embodiment of the present invention, the modified strain is derived from Trichoderma sp. containing deleted or disrupted genes for CBHI and/or CBHII thereby being unable to produce catalytically active cellobiohydrolase. The cellulase enzymes produced by such an organism will be enriched in endoglucanases and include no more than 20% cellobiohydrolases based upon the combined weight of cellulase proteins which it produces. It is particularly preferred that the modified strain is unable to produce catalytically active CBHI as this enzyme forms the greatest proportion o any component of whole cellulase from Trichoderma sp. In instances where only production of EGIII is desired, it is further preferred that such a modified strain contains deleted or disrupted genes for EGI and EGII so as to be unable to produce catalytically active EGI and/or EGII.

Alternatively, the modified strain can additionally contain recombinant DNA allowing expression and secretion of truncated catalytic cores of either EGI or EGII. While not wishing to be bound by theory, it is believed that the presence of a cellulose binding domain on a cellulase may be responsible for certain undesirable properties observed when animals are fed feed supplemented with cellulase, e.g. increased gut viscosity. Accordingly, by removing the cellulose binding domain and retaining an intact cellulase core, it is possible to limit or eliminate these properties.

Before describing methods of producing such truncated endoglucanases, the following provides a detailed description of the drawings which is necessary to understand these production techniques.

FIG. 1 depicts the genomic DNA and amino acid sequence of EGI. The signal sequence begins at base pair 113 and ends at base pair 178 (Seq ID No. 13). The catalytic core domain begins at base pair 179 through 882 of exon one, and base pair 963 through base pair 1379 of the second exon (Seq ID No. 5). The linker region begins at base pair 1380 and ends at base pair 1460 (Seq ID No. 9). The cellulose binding domain begins at base pair 1461 and ends a: base pair 1616 (Seq ID No. 1). Seq ID Nos. 14, 6, 10 and 2 represent the amino acid sequence of EGI signal sequence, catalytic core domain, linker region and binding domain, respectively.

FIG. 2 depicts the genomic DNA and amino acid sequence of EGII. The signal sequence begins at base pair 262 and ends at base pair 324 (Seq ID No. 15). The cellulose binding domain begins at base pair 325 and ends at base pair 432 (Seq ID No. 3). The linker region begins at base pair 433 and ends at base pair 534 (Seq No. 11). The catalytic core domain begins at base pair 535 through base pair 590 in exon one, and base pair 765 through base pair 1689 in exon two (Seq ID No. 7). Seq ID Nos. 16, 4, 12 and 8 represent the amino acid sequence of EGII signal sequence, binding domain, linker region and catalytic core domain, respectively.

FIG. 3 depicts the genomic DNA and amino acid sequence of EGIII. The signal sequence begins at base pair 151 and ends at base pair 198 (Seq ID No. 19). The catalytic core domain begins at base pair 199 through base pair 557 in exon one, base pair 613 through base pair 833 in exon two and base pair 900 through base pair 973 in exon three (Seq ID No. 17). Seq ID Nos. 20 and 18 represent the amino acid sequence of EGIII signal sequence and catalytic core domain, respectively.

As mentioned above, the one or more endoglucanases present in the enzyme feed additive of the present invention may be truncated EG derivatives such as EGI which lacks the cellulose binding domain (which can be termed EGIcore) and/or EGII also lacking the cellulose binding domain. These derivatives are prepared by recombinant methods by transforming into a host cell, a DNA construct comprising at least a fragment of DNA encoding a portion or all of the core region of the endoglucanases, for example, EGI or EGII functionally attached to a promoter, growing the host cell to express the truncated endoglucanase, derivative of truncated endoglucanase or covalently linked truncated endoglucanase domain derivatives of interest. The resulting truncated endoglucanase can be used once separated from the microrganism cells as a feed additive. As an alternative, the truncated endoglucanase, or derivative thereof may in addition be purified to substantial homogeneity prior to use.

The following Reference Examples 1 and 2 are provided in order to illustrate techniques for producing endoglucanase enriched enzyme compositions by transforming and growing genetically modified microorganisms.

Reference Example 1

Cloning and Expression of EGI Core Domain Using its Own Promoter, Terminator and Signal Sequence.

Part 1. Cloning

Figures 1, 1C:
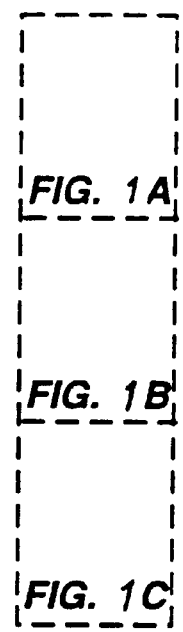
Figure 4A:
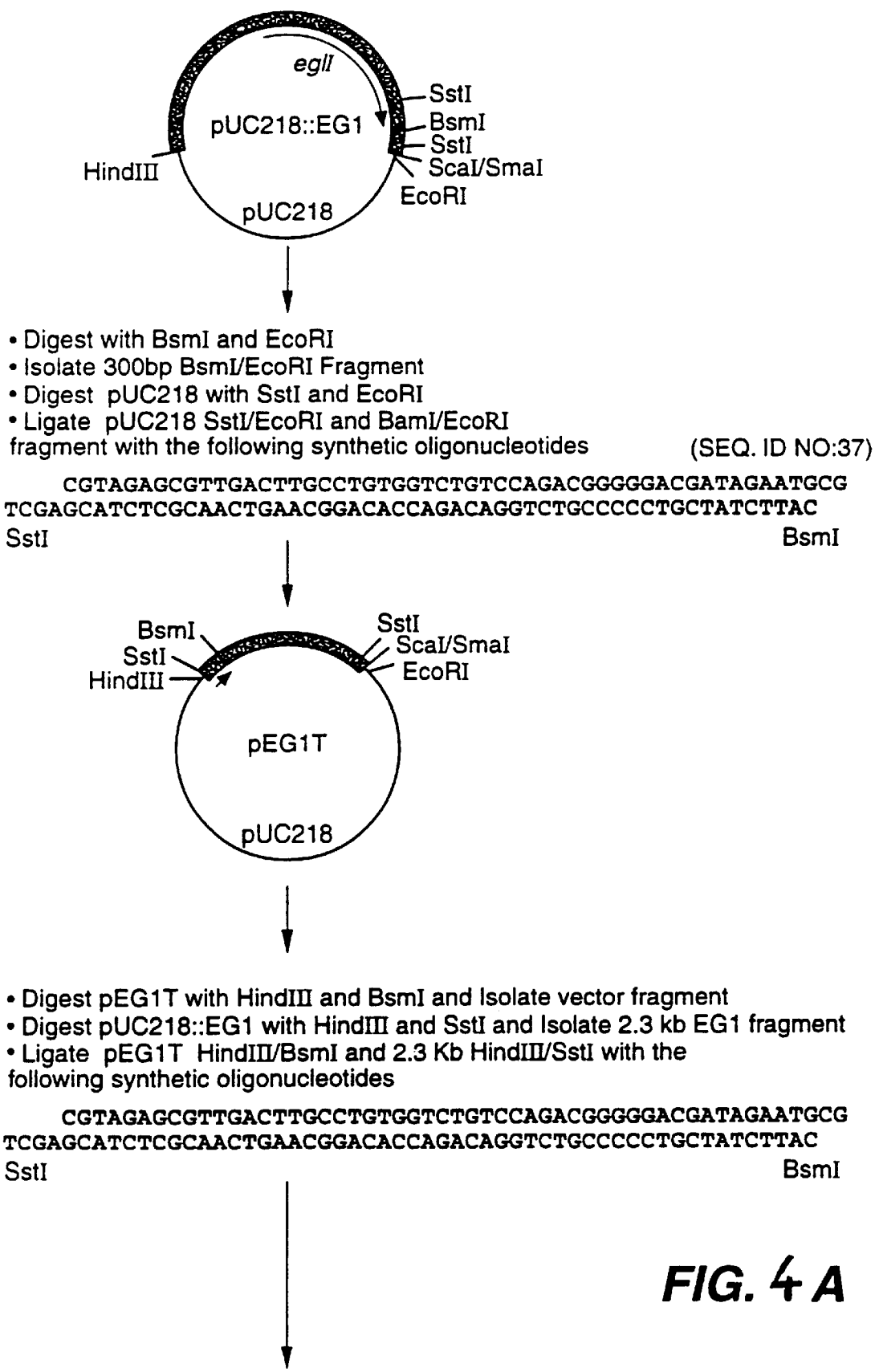
FIG. 4 illustrates the construction of EGI core domain expression vector (Seq ID No. 21).

The complete egl1 gene used in the construction of the EG1 core domain expression plasmid, pEGID3'pyr, was obtained from the plasmid pUC218::EG1. (See FIG. 4.) The 3' terminator region of egl1 was ligated into pUC218 (Korman, D. et al Curr Genet 17:203–212, 1990) as a 300 bp BsmI–EcoRI fragment (the BsmI site is at 46 bp 3' of the egl1 stop codon) along with a synthetic linker designed to replace and cellulose binding domain of egl1 with a stop codon and continue with the first 46 bp of the egl1 terminator sequence. The resultant plasmid, pEG1T, was digested with HindIII and BsmI and the vector fragment with the egl1 terminator was isolated from the digest by agarose gel electrophoresis followed by electroelution. The egl1 gene promoter sequence and core domain of egl1 were isolated from pUC218::EG1 as a 2.3 kb HindIII-SstI fragment and ligated with the same synthetic linker fragment and the HindIII-BsmI digested pEG1T to form pEG1D3'.

The net result of these operations is to replace the 3' intron and cellulose binding domain of egl1 with synthetic oligonucleotides of 53 and 55 nt. These place a TAG stop codon after serine 415 and thereafter continued with the egl1 terminator up to the BsmI site.

Next, the $T.$ $longibrachiatum$ selectable marker, pyr4, was obtained from a previous clone p219M (Smith et al 1991), as an isolated 1.6 kb EcoRI-HindIII fragment. This was incorporated into the final expression plasmid, pEG1D3'pyr, in a three way ligation with pUC18 plasmid digested with EcoRI and dephosphorylated using calf alkaline phosphatase and a HindIII-EcoRI fragment containing the egl1 core domain from pEGID3'.

Part 2. Transformation and Expression

A large scale DNA prep was made of pEG1D3'pyr and from this the EcoRI fragment containing the egl1 core domain and pyr4 gene was isolated by preparative gel electrophoresis. The isolated fragment was transformed into a strain (1A52pyr13) in which the cbh1, cbh2, egl1 and egl2 genes had been deleted and which was pyr4$^-$ (described in WO 92/06209) and stable transformants were identified.

To select which transformants expressed egl1 core domain the transformants were grown up in shake flasks under conditions that favored induction of the cellulase genes (Vogel's medium+1% lactose). After 4–5 days of growth, protein from the supernatants was concentrated and either 1) run on SDS polyacrylamide gels prior to detection of the EGI core domain by Western analysis using anti-EGI polyclonal antibodies or 2) the concentrated supernatants were assayed directly using Remazol Brilliant Blue (RBB) carboxy methyl cellulose as an endoglucanase specific substrate and the results compared to the parental strain (1A52) as a control. Transformant candidates were identified as possibly producing a truncated EGI core domain protein. Genomic DNA and total mRNA was isolated from these strains following growth on Vogels+1% lactose and Southern and Northern blot experiments performed using an isolated DNA fragment containing only the egl1 core domain. These experiments demonstrated that transformants could be isolated having a copy of the egl1 core domain expression cassette integrated into the genome of 1A52 and that these same transformants produced egl1 core domain mRNA.

One transformant was then grown using media suitable for cellulase production in Trichoderma well known in the art that was supplemented with lactose (Warzymoda, M. et al 1984 French Patent No. 2555603) in a 14L fermentor. The resultant broth was concentrated and the proteins contained therein were separated by SDS polyacrylamide gel electrophoresis and the EGI core domain protein identified by Western analysis. It was subsequently estimated that the protein concentration of the fermentation supernatant was about 5–6 g/L of which approximately 1.7–4.4 g/L was EGI core domain based on CMCase activity. This value is based on an average of several EGI core fermentations that were performed.

In a similar manner, any other endoglucanase whether truncated or not or derivative thereof may be produced by procedures similar to those discussed above. Thus production of EGI can be achieved by using similar techniques except that deletion of the cellulose binding domain is omitted. Corresponding techniques can be used to produce complete EGII, EGIII, and EGII from which the cellulose binding domain is omitted.

Reference Example 2

Purification of EGI and EGII Catalytic Cores

Part 1. EGI Catalytic Core

The EGI core was purified in the following manner. The concentrated (UF) broth was diluted to 14 mg/ml in 23 mM Na Acetate pH 5.0. Two hundred grams of avicel cellulose gel (FMC Bioproducts, Type PH-101) was added to the diluted EGI core broth and mixed at room temperature for forty five minutes. The avicel was removed from the broth by centrifugation, resulting in an enriched EGI core solution. This solution was then buffer exchanged into 10 mM TES pH 7.5 using an Amicon stirred cell concentrator with a PM 10 membrane (diaflo ultra filtration membranes, Amicon Cat #13132MEM 5468A). The EGI core sample was then loaded onto an anion exchange column (Q-sepharose fast flow, Pharmacia Cat #17–0510-01) and eluted in a salt gradient from 0 to 0.5M NaCl in 10 mM TES pH 7.5. The fractions which contained the EGI core were combined and concentrated using the Amicon stirred cell concentrator mentioned above.

Part 2. EGII Catalytic Core

It is contemplated that the purification of the EGII catalytic core is similar to that of EGII cellulase because of its similar biochemical properties. The theoretical pI of the EGII core is less than a half a pH unit lower than that of EGII. Also, EGII core is approximately 80% of the molecular weight of EGII. Therefore, the following purification protocol is based on the purification of EGII. The method may involve filtering the UF concentrated broth through diatomaceous earth and adding (NH4)2S04 to bring the solution to 1M (NH4)2S04. This solution may then be loaded onto a hydrophobic column (phenyl-sepharose fast flow, Pharmacia, cat #17-0965-02) and the EGII may be step eluted with 0.15 M (NH4)2S04. The fractions containing the EGII core may then be buffer exchanged into citrate-phosphate pH 7, 0.18 mOhm. This material may then be loaded onto a anion exchange column (Q-sepharose fast flow, Pharmacia, cat. #17-0510-01) equilibrated in the above citrate-phosphate buffer. It is expected that EGII core will not bind to the column and thus be collected in he flow through.

The present invention will be explained in more detail by way of the following further Reference Example 3 and Example 1. In the Example 1, reference is made to units of β-glucanase activity. This activity is measured by the following assay.

One unit of β-glucanase activity is the amount of enzyme which liberates one pmol of reducing sugars (expressed as glucose equivalents) from the substrate in one minute under the conditions described.

Reagents 1. 1.0% (w/v) β-glucan Substrate

Moisten 1.0 g of mixed-linked β-(1,3)(1,4)-glucan (Biocon Biochemicals Ltd.) with 10 ml of ethanol. Add about 80 ml of distilled water and warm up to boil. Continue boiling with vigorous stirring until β-glucan is dissolved and a turbid solution is obtained. Cool the turbid solution to room temperature continuously stirring and adjust the β-glucan concentration to 1.0% (w/w) by adding distilled water. Filter through a glass fibre filter paper.

The substrate can be used immediately. The substrate is usable for two days if stored in a cold room.

2. 0.1 M Sodium Acetate Buffer, pH 5.0

A. Dissolve 8.2 g of anhydrous sodium acetate in distilled water and fill to 1000 ml with distilled water.

B. Dissolve 6.0 g of glacial acetic acid in distilled water and fill to 1000 ml with distilled water.

Adjust the pH of solution A to 5.0 with solution B.

3. Dinitrosalicylic Acid (DNS) Reagent

Suspend 20.0 g of 3,5-dinitrosalicylic acid in about 800 ml of distilled water. Add gradually 300 ml of sodium hydroxide solution (32.0 g of NaOH in 300 ml of distilled water) while stirring continuously. Warm the suspension in a water bath (the temperature may not exceed +48° C.) while stirring until the solution is clear. Add gradually 600 g of potassium sodium tartrate. Warm the solution (the temperature may not exceed +48° C.) if needed until solution is clear.

Fill to 2000 ml with distilled water and filter through a coarse sintered glass filter.

Store in a dark bottle at room temperature. The reagent is stable for a maximum of 6 months.

Procedure 1. Enzyme Sample

Equilibrate 1 ml of enzyme dilution (in 0.1 M sodium acetate buffer, pH 5.0) at +30° C. Add 1 ml of β-glucan substrate, stir and incubate at +30° C. for exactly 10 minutes. Add 3 ml of DNS-reagent, stir and boil the reaction mixture for exactly 5 minutes. Cool the reaction mixture in a cold water bath to room temperature and measure the absorbance at 540 nm against distilled water.

2. Enzyme Blank

Incubate 1 ml of β-glucan substrate at +30° C. for 10 minutes. Add 3 ml of DNS-solution and stir. Add 1 ml of enzyme dilution (in 0.1 M sodium acetate buffer, pH 5.0) and stir. Boil the mixture for exactly 5 minutes. Cool the reaction mixture in cold water bath to room temperature and measure the absorbance at 540 nm against distilled water.

The absorbance difference between the enzyme sample and the enzyme blank should be 0.3–0.5.

3. Standard Curve

Prepare standard solutions from anhydrous glucose in distilled water. Glucose concentration in the standards should be 0.1–0.6 mg/ml. Pipette 1 ml of glucose standard solution, 1 ml of distilled water and 3 ml of DNS-reagent into a test tube. Stir and boil for exactly 5 minutes. Cool in a cold water bath to room temperature and measure the absorbance at 540 nm against standard blank. In the standard blank, glucose solution is replaced by 1 ml of distilled water. Otherwise standard blank is treated like glucose standard.

Plot glucose concentration as a function of absorbance. New standard curve is prepared for every new DNS-reagent.

Calculation

The β-glucanase activity of the sample is calculated according to the following equation:

$$\text{Activity (U/g)} = \frac{([A(X) - A(O)] \times k + C_1) \times 1000 \times Df}{MW_{glu} \times t}$$

wherein:
A(X)=absorbance of the enzyme sample
A(O)=absorbance of the enzyme blank
k=the slope of the standard curve
C.=the intercept of glucose standard curve
1000=factor, mmol->μmol
Df=dilution factor (ml/g)
$MW_{glu}$=molecular weight of glucose(180.16 mg/mmol)
t=reaction time (10 minutes)

The Reference Example 3 makes reference to the measurement of the viscosity reducing activity of β-glucanase. This activity is measured by the following assay.

Principle

β-glucanase catalyses the hydrolysis of β-glucan which results in reduction of viscosity of β-glucan solution. Reciprocal specific viscosity as a function of time is linear function at the initial moment of the reaction. Using the slope of the linear curve β-glucanase activity can be determined. Reciprocal specific viscosity is determined using a capillary viscosimeter.

Apparatus

Ostwald capillary viscosimeter (Brand, No 11, 75–100 sec)
Water bath controlled at 30° C.
Magnetic stirrer
Stop Watch
Glassinter filters no 3 and 4
Magnetic stirrer with hotplate

Reagents 1. 0.5 M Acetate Buffer, pH 4.0

Dilute 30 g of glacial acetic acid (BDH AnalaR 10001) into 900 ml of distilled water.
Adjust the pH to 4.0 with 2.5 g of NaOH (Merck 6498). Fill with distilled water into 1000 ml.

2. 0.05 M Acetate Buffer, pH 4.0

Dilute 100 ml of 0.5 M acetate buffer, pH 4.0 into 800 ml of distilled water. Adust pH if needed to 4.0 with 1 M NaOH or glacial acetic acid. Fill to 1000 ml with distilled water. Filtrate through glassinter filter no 4.

3. β-glucan Solution

Weigh 1.0 g mixed-linked β-(1,3)(1,4)-glucan (Biocon Biochemicals) in a tared beaker. Add approx. 6 ml of ethanol and mix with metallic mixing rod until the mixed-linked β-glucan has become totally wet. Add approx. 80 ml of distilled water, mix with magnetic stirrer and warm up solution to boil. Keep boiling until the mixed-linked β-glucan has totally dissolved. Ensure that there is no material on the walls of the beaker. Cool the solution to room temperature while continuously stirring. Add 10 ml of 0.5 M acetate buffer, pH 4.0. If needed adjust pH to 4.0 with 1 M NaOH or glacial acetic acid. Add distilled water until the total weight of the substrate solution is 100 g. Filtrate with glassinter filter no 3. Store the substrate solution maximum for two days at +4° C.

Procedure

1. Determination of Reciprocal Specific Viscosity

Before activity determination ensure that viscosimeter is clean by rinsing with distilled water and acetone (in this sequence). Dry the viscosimeter by removing acetone with compressed air or in vacuum.
All samples, substrate solution and viscosimeter have to be equilibrated at 30 ° C. for at least 15 minutes before determination.

Reciprocal specific viscosity follows equation 1

$$1/\mu_{sp} = \frac{dT_0}{dT_s - dT_0} \quad \text{(Equation 1)}$$

whereas
$1/\mu_{sp}$=reciprocal specific viscosity
$dT_0$=falling-time of acetate buffer (in seconds)
$dT_s$=falling-time of sample solution (in seconds)
The falling-time for solutions follow equation 2

$$dT_i = T_2 - T_1 - h \quad \text{(Equation 2)}$$

where
$dT_i$=falling-time of solutions
$T_2-T_1$=time used by the solution to fall between upper and lower marks in the capillary (in seconds)
h=Hagenbach factor

| Hagenbach factors: | |
|---|---|
| Falling-time ($dT_i$) | |
| s | h |
| <54.2 | 1.0 |
| 54.3–57.3 | 0.9 |
| 57.4–60.5 | 0.8 |
| 60.6–65.5 | 0.7 |
| 65.6–70.8 | 0.6 |
| 70.9–78.5 | 0.5 |
| 78.6–88.9 | 0.4 |
| 89.0–105 | 0.3 |
| 105–135 | 0.2 |
| 135–240 | 0.1 |
| >240 | 0 |

Start the determination of the falling-time with a clean and dry viscosimeter by pumping 7.5 ml of solution to the capillary so that the surface of the solution exceeds the upper mark of the capillary. Determine with stop watch the time needed for the solution to fall between upper and lower marks in the capillary.

2. Determination of Falling-time for Acetate Buffer

Determine the falling-time ($dT_0$) for 0.05 M acetate buffer, pH 4.0, as described above whenever β-glucanase activity is determined.

3. Adjustment of β-glucan Solution

The initial reciprocal specific viscosity in the hydrolysis of β-glucan has to be 0.13. The viscosity in the β-glucan solution varies from batch to batch and this has to be compensated by varying the ratio of β-glucan solution and sample so that the initial viscosity is correct.

Make 5 different β-glucan/0.05 M acetate buffer, pH 4.0, mixtures by pipetting β-glucan (A) 5.0–6.5 ml and respectively 2.5–1.0 ml of 0.05 M acetate buffer, pH 4.0, to make the total volume of each mixture to be 7.5 ml. Determine the viscosities of these solutions and calculate the reciprocal specific viscosities.

Plot the reciprocal specific viscosity as a function of β-glucan. From the graph determine the amount of β-glucan that corresponds to a reciprocal specific viscosity value of 0.13. This β-glucan amount will be used later on in all β-glucanase activity determinations with this β-glucan solution.

Initial viscosity of β-glucan solution has to be determined whenever β-glucanase activity is determined.

4. Determination of β-glucanase Activity

Pipette β-glucan volume (A) determined as described above to the test tube and equilibrate at 30° C. for at least 15 minutes. Add V ml (V=7.5 ml–A) of enzyme sample diluted in 0.05 M acetate buffer, pH 4.0 and equilibrated at 30° C. for at least 15 minutes. Start the stop watch. Mix the solution properly and transfer it to the viscosimeter. Determine falling-time $dT_s$ 4–5 times during 20–30 minutes from the mixing of the solutions.

The determinations have to be done from at least two different dilutions and with at least 3 parallel determinations from each dilution. Proper dilution of the sample depends on enzyme mixture product and end feed to be assayed. The dilutions are indicated separately. For enzyme mixtures the total dilution factor is typically 1/2000–1/15000 and for end feeds 1/5–1/20.

Calculations

Calculate the reciprocal specific viscosities according to equation 1. Plot the reciprocal specific viscosity as a function of hydrolysis time (in seconds).

β-glucanase activity is determined as an increase of reciprocal specific viscosity (IRV) in one minute, equation 3.

$$\beta\text{-glucanase activity } (IRVU/g) = k \times D \times 60 / V \quad \text{(Equation 3)}$$

where
k=slope of the curve
D=total dilution factor
60=conversion factor, s->min
V=sample volume

Literature

The Institute of Brewing (1979) J. Inst. Brew, 85, 92–94.

Analyse av β-glukanaseaktivitet ved viskosimetrisk metode, Norges Veterinaerhogskole.

Reference Example 3

The first trial which was undertaken was to compare the efficacy in vitro of several different cellulases having an enriched content of endoglucanases in comparison with whole cellulase. Thus, seven different enzyme preparations were prepared the first from naturally occurring *T. longibrachiatum* and the second-seventh from genetically modified strains thereof in accordance with the following Table 1:

TABLE 1

| Enzyme Preparation | Strain Genotype |
| --- | --- |
| Whole cellulase | EGI$^+$ EGII$^+$ EGIII$^+$ CBNI$^+$ CHBII$^+$ |
| Enriched EGI | EGI$^{+++}$ EGII$^+$ EGIII$^+$ CBHI$^-$ CHBII$^+$ |
| Enriched EGIΔcbd | EGIΔcbd$^+$ EGI$^-$ EGII$^+$ EGII$^+$ EGIII$^+$ CBHI$^-$ CBHII$^+$ |
| Enriched EGII | EGI$^+$ EGII$^{+++}$ EGIII$^+$ CBHI$^+$ CBHII$^-$ |
| Enriched EGIII | EGI$^+$ EGII$^-$ EGIII$^+$ CBHI$^+$ CBHII$^-$ |
| Purified EGIII | EGI$^+$ EGII$^+$ EGIII$^+$ CBHI$^-$ CBHII$^-$ |

In the above Table 1, the strain producing enriched EGI contains multiple EGI encoding genes. Similarly, the strains producing enriched EGII and EGIII respectively contain multiple copies of the EGII and EGIII encoding genes.

The enriched EGI, enriched EGII, enriched EGIII and purified EGIII enzyme preparations were obtained by following the procedures described in PCT WO 92/06209. Purified EGIII was the same as enriched EGIII, except that the supernatant containing the secreted EGIII was subjected to the PEG purification procedure described in U.S. Pat. No. 5,328,841 to remove xylanase activity. Truncated EGI core was produced according to the techniques described in Reference Example 1 and purified in accordance with Reference Example 2.

The viscosity reducing activity on soluble mixed-linked barley β-glucan was measured for each of the above enzyme preparations in accordance with the assay described above.

Figure 5:
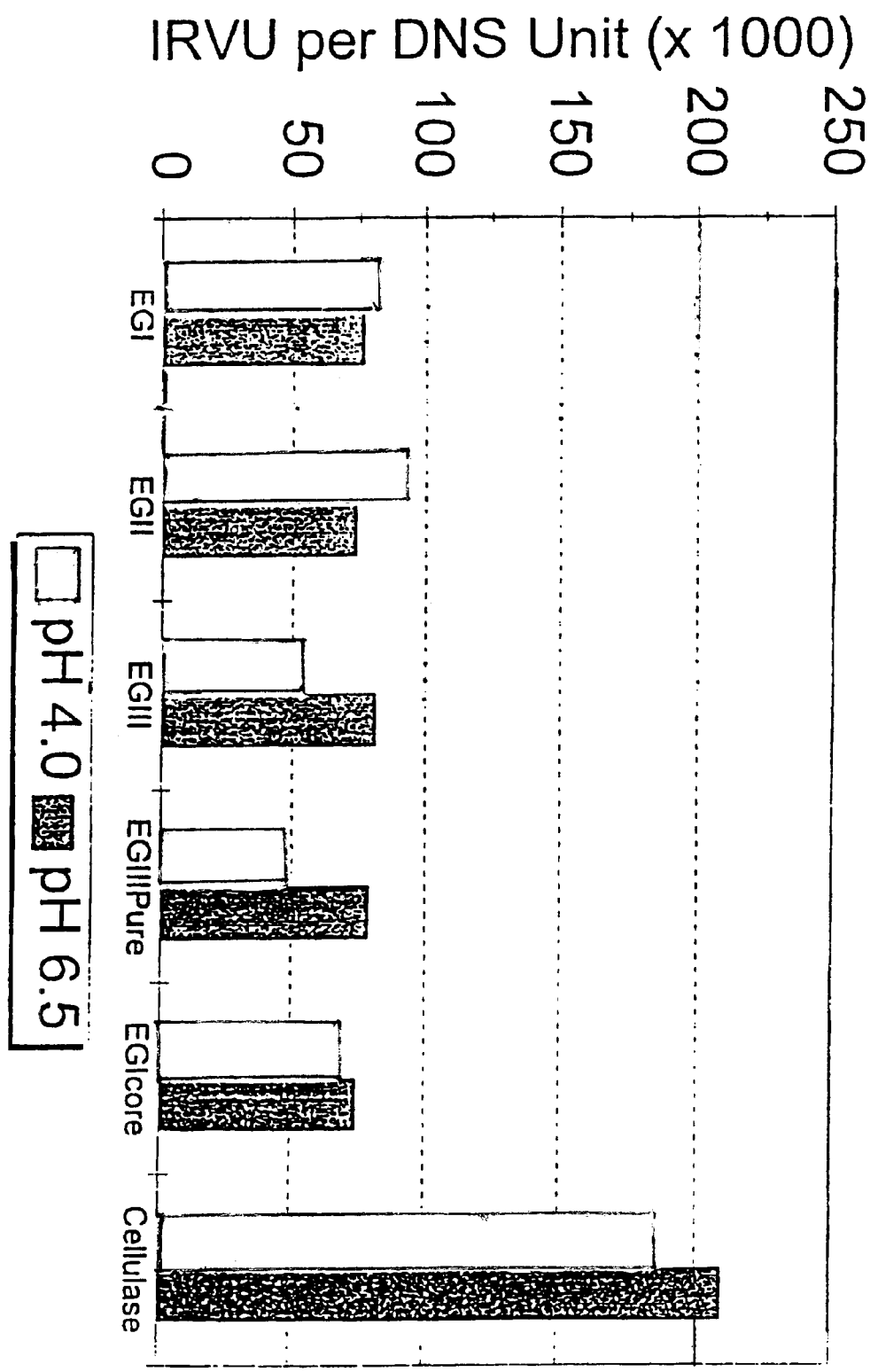
FIG. 5 is a graph demonstrating the initial viscosity-reducing activity of whole cellulase and various enriched endoglucanase preparations at different pHs.

The results of this testing are illustrated in the graph of FIG. 5. Since *T. longibrachiatum* β-glucanase is dosed as a feed additive on the basis of activity measured by the DNS reducing sugar assay method, enzyme addition for the viscosity-reducing activity assay was standardised by this procedure.

The results illustrated in FIG. 5 demonstrate that the viscosity-reducing activity of whole cellulase is significantly higher than that of each of the enriched endoglucanase preparations regardless of pH.

Example 1

Thirteen groups of broiler chickens, each initially including a minimum of 49 chickens, were fed with the barley-based feed set out in Table 2 between 8 and 21 days of age. Feed intake and body weight gain were measured between 8 and 21 days.

TABLE 2

| Ingredients | Percent | Weight |
| --- | --- | --- |
| Barley | 58.56% | 585.63 |
| Soybean ml 48 | 31.63% | 316.26 |
| Soy oil | 6.07% | 60.65 |
| Salt | 0.29% | 2.90 |
| DL Methionine | 0.28% | 2.76 |
| Lysine HCl | 0.04% | 0.44 |
| Limestone | 1.41% | 14.06 |
| Dicalcium Phos | 1.23% | 12.31 |
| VIT/MIN | 0.50% | 5.00 |
| TOTAL | 100.00% | 1000.00 |

The nutritional value of the above feed can be subjected to computer analysis using for example the programme "Format" available from Format International. This provides an analysis of the nutrient content of the feed including for example the expected nutritional levels of various metabolites. The results of such an analysis for the feed of Table 2 is set out in the following Table 3.

TABLE 3

| Barley-Based Diet | | |
| --- | --- | --- |
| Nutrient | Target | Value |
| Crude protein % | 22.00 | 22.00 |
| Poult ME kcal/kg | 3000.00 | 3000.00 |
| Pig DE Kcal | | 3363.16 |
| Calcium % | 0.90 | 0.90 |
| Phos % | | 0.66 |
| Avail Phos % | 0.40 | 0.40 |
| Fat % | | 7.28 |
| Fibre % | | 4.00 |
| Met % | | 0.58 |
| Cys % | | 0.37 |
| Met + Cys % | 0.95 | 0.95 |

TABLE 3-continued

Barley-Based Diet

| Nutrient | Target | Value |
|---|---|---|
| Lys % | 1.25 | 1.25 |
| His % |  | 0.52 |
| Tryp % | 0.24 | 0.30 |
| Thr % | 0.80 | 0.82 |
| Arg % | 1.40 | 1.44 |
| Iso % |  | 1.01 |
| Leu % |  | 1.59 |
| Phe % |  | 1.11 |
| Val % |  | 1.10 |
| Gly % |  | 0.99 |
| Phe + Tyr % |  | 1.89 |
| Na % | 0.15 | 0.15 |
| Cl % |  | 0.29 |
| K % |  | 0.96 |
| Linoleic acid % | 1.00 | 3.00 |
| Na + K + HCl |  | 2.29 |

The barley-based feeds fed to twelve of the groups of chickens were supplemented by varying amounts of each of the enzyme preparations set out in the above Table 1. Each of the enzyme preparations was tested at a β-glucanase activity concentration of 120 units/kg of the feed and 240 units/kg of the feed. The β-glucanase activity was measured using the β-glucanase activity assay described above. The diet of the thirteenth group, the control group, was not supplemented with any of the enzyme preparations.

Results of these various tests are set out in the following Tables 4 and 5. The results set out in Table 4 are for diets supplemented with 120 units of β-glucanase activity per kg of feed whereas the results set out in Table 5 are for feeds supplemented with 240 units of β-glucanase activity per kg of feed. The results set out in the Tables 4 and 5 provide the body weight gain, the feed conversion ratio and the viscosity in the gastrointestinal region of the various groups of broiler chickens. The results have been adjusted for mortality.

TABLE 4

|  | BWG (g) | FCR | Viscosity (cps) |
|---|---|---|---|
| Control | 329 | 1.72 | 15.3 |
| Enriched EGI | 358 | 1.60 | 12.6 |
| Enriched EGI.Δcbd | 437 | 1.42 | 10.5 |
| Enriched EGII | 396 | 1.50 | 13.6 |
| Enriched EGIII | 356 | 1.66 | 6.0 |
| Purified EGIII | 332 | 1.85 | 7.9 |
| Complete Cellulase | 381 | 1.62 | 10.3 |

TABLE 5

|  | BWG (g) | FCR | Viscosity (cps) |
|---|---|---|---|
| Control | 329 | 1.72 | 15.3 |
| Enriched EGI | 376 | 1.60 | 14.5 |
| Enriched EGI.Δcbd | 395 | 1.57 | 5.6 |
| Enriched EGII | 377 | 1.70 | 11.6 |
| Enriched EGIII | 423 | 1.54 | 8.1 |
| Purified EGIII | 401 | 1.56 | 7.7 |
| Complete Cellulase | 404 | 1.66 | 6.4 |

From the above results, it can be seen that the body weight gain, feed conversion ratio and viscosity for the control group without enzyme supplementation were relatively poor. In comparison with the results for whole cellulase, enriched EGI is more effective in terms of FCR when used at a dosage of 240 units/kg of feed. The same is also true for enriched EGIII and purified EGIII. On the other hand, enriched EGII provides superior results at 120 units/kg of feed. Finally, the most preferred enzyme preparation, which is the enriched EGI.Δcbd provides superior results at both 120 and 240 units/kg of feed. This enzyme preparation deleted for the cellulose binding domain provides superior results at both concentrations tested as compared to enriched natural type EGI. These results also strongly suggest that the different enzyme preparations have different dose optima in terms of their effects on body weight gain and feed conversion ratios.

By comparing the results of Reference Example 3 and Example 1, it can be seen that different results are obtained between in vitro and in vivo testing. Thus, in the in vitro testing of Reference Example 3, the viscosity reducing activity of whole cellulase was higher than that for the enriched preparations of EGI, EGII, EGIII and EGI.Δcbd.

In contrast, the in vivo test results of Example 1 indicate that each of the enzyme preparations tested has at least one advantageous characteristic of improved body weight gain, feed conversion ratio and/or reduced viscosity in the gastrointestinal region as compared to whole cellulase at both concentrations tested. The preferred enzyme preparations are EGI.Δcbd and EGIII.

The effects demonstrated above of reducing feed conversion ratios and/or gastrointestinal viscosities can also be obtained when feeds prepared in accordance with the present invention but based upon other cereals such as wheat, triticale, rye and maize are fed to other animals such as turkeys, geese, ducks, pigs, sheep and cattle, as well as chickens.

What is claimed is:

1. An enzyme-based feed additive comprising
   (a) a cellulase selected from the group consisting of i) a truncated cellulase core of endoglucanase III, ii) a truncated cellulase core of endoglucanase I which lacks the cellulose binding domain, iii) a endoglucanase II which lacks the cellulose binding domain, and iv) the truncated cellulase core of iii);
   (b) 0–20% by weight, based upon the content of cellulase proteins in the additive, of a cellobiohydrolase; and
   (c) one or more additional enzymes selected from a xylanase, a protease, an α-amylase, a glucoamylase, a lipase, a pectinase, a mannanase, an α-galactosidase, an α-arabinofurosidase, and a phytase.

2. An enzyme-based feed additive according to claim 1, wherein the xylanase is the high pI xylanase of T. longibrachiatum.

3. The enzyme-based feed additive of claim 1, wherein the additive is free of any cellobiohydrolase.

4. An enzyme-based feed additive according to claim 1, wherein the xylanase is the low pI xylanase of T. longibrachiatum.

5. The enzyme-based feed additive of claim 1, wherein the additional enzyme is a xylanase.

6. The enzyme-based feed additive of claim 1, wherein the additional enzyme is a protease.

7. The enzyme-based feed additive of claim 1, wherein the cellulase is a truncated cellulase core of endoglucanase III.

8. The enzyme-based feed additive of claim 1, wherein the cellulase is endoglucanase II which lacks the cellulose binding domain.

9. The enzyme-based feed additive of claim 1, wherein the cellulase is the truncated cellulase core of endoglucanase I which lacks a cellulose binding domain.

10. The enzyme-based feed additive of claim 1, wherein the endoglucanase has the amino acid sequence illustrated in SEQ ID NO. 10.

11. The enzyme-based feed additive of claim 1, wherein the endoglucanase has the amino acid sequence illustrated in SEQ ID NO. 8.

12. The enzyme-based feed additive of claim 1, wherein the endoglucanase has the amino acid sequence illustrated in SEQ ID NO: 18.

13. A cereal-based animal feed comprising
    (a) at least one cereal selected from barley, soya, wheat, triticale, rye and maize and
    (b) an enzyme-based feed additive comprising
        (i) a cellulase selected from the group consisting of
            a) a truncated cellulose core of endoglucanase III,
            b) a truncated cellulase core of endoglucanase I which lacks the cellulose binding domain,
            c) a endoglucanase II which lacks the cellulose binding domain, and
            d) the truncated cellulase core of c); and
        (ii) 0–20% by weight, based upon the content of cellulase proteins in the additive, of a cellobiohydrolase.

14. A method of reducing the feed conversion ratio of a feed comprising applying an enzyme-based feed additive comprising
    (a) a cellulase selected from the group consisting of
        i) a truncated cellulase core of endoglucanase III,
        ii) a truncated cellulase core of endoglucanase I which lacks the cellulose binding domain,
        iii) a endoglucanase II which lacks the cellulose binding domain, and
        iv) the truncated cellulase core of iii); and
    (b) 0–20% by weight, based upon the content of cellulase proteins in the additive, of a cellobiohydrolase to a feed.

15. The method of claim 14, wherein the feed is a cereal-based feed.

16. The method according to claim 14, wherein the additive is free of any cellobiohydrolase.

17. The method according to claim 15, wherein the cereal is selected from the group consisting of barley, maize and soya.

18. An enzyme-based feed additive comprising
    (a) an endoglucanase I which lacks a cellulose binding domain or a derivative endoglucanase I which lacks a cellulose binding domain that retains its endoglucanase activity,
    (b) 0–20% by weight, based upon the content of cellulase proteins in the additive, of a cellobiohydrolase, and
    (c) one or more additional enzymes selected from a xylanase, a protease, an α-amylase, a glucoamylase, a lipase, a pectinase, a mannanase, an α-galactosidase, an α-arabinofurosidase and a phytase. endoglucanase II which lacks the cellulose binding domain.

19. The enzyme-based feed additive of claim 18, wherein the additive is free of any cellobiohydrolase.

20. An enzyme-based feed additive comprising
    (a) an endoglucanase II which lacks a cellulose binding domain or a derivative endoglucanase II which lacks a cellulose binding domain that retains its endoglucanase activity,
    (b) 0–20% by weight, based upon the content of cellulase proteins in the additive, of a cellobiohydrolase, and
    (c) an enzyme selected from the group consisting of xylanases, proteases, α-amylases, glucoamylases, lipases, pectinases, mannanases, α-galactosidases, α-arabinofurosidases and phytases.

21. The enzyme-based feed additive of claim 20, wherein the enzyme is a xylanase.

* * * * *

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 158 base pairs
      (B) TYPE: nucleic acid

```
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1..82, 140..158)

(xi) SEQUENCE DESCRIPTION: SEQ ID NO: 1:

CAC TGG GGG CAG TGC GGT GGC ATT GGG TAC AGC GGG TGC AAG ACG TGC        48
His Trp Gly Gln Cys Gly Gly Ile Gly Tyr Ser Gly Cys Lys Thr Cys
 1               5                  10                  15

ACG TCG GGC ACT ACG TGC CAG TAT AGC AAC GAC   T GTTCGTATCC             92
Thr Ser Gly Thr Thr Cys Gln Tyr Ser Asn Asp
            20                  25

CCATGCCTGA CGGGAGTGAT TTTGAGATGC TAACCGCTAA AATACAG  AC TAC TCG       147
                                                       Tyr Tyr Ser
                                                                30

CAA TGC CTT TA                                                        158
Gln Cys Leu (2) INFORMATION FOR SEQ ID NO: 2:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO: 2:

His Trp Gly Gln Cys Gly Gly Ile Gly Tyr Ser Gly Cys Lys Thr Cys
 1               5                  10                  15

Thr Ser Gly Thr Thr Cys Gln Tyr Ser Asn Asp Tyr Tyr Ser Gln Cys
            20                  25                  30

Leu (2) INFORMATION FOR SEQ ID NO: 3:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..108

(xi) SEQUENCE DESCRIPTION: SEQ ID NO: 3:

CAG CAG ACT GTC TGG GGC CAG TGT GGA GGT ATT GGT TGG AGC GGA CCT        48
Gln Gln Thr Val Trp Gly Gln Cys Gly Gly Ile Gly Trp Ser Gly Pro
 1               5                  10                  15

ACG AAT TGT GCT CCT GGC TCA GCT TGT TCG ACC CTC AAT CCT TAT TAT        96
Thr Asn Cys Ala Pro Gly Ser Ala Cys Ser Thr Leu Asn Pro Tyr Tyr
            20                  25                  30

GCG CAA TGT ATT                                                       108
Ala Gln Cys Ile
        35

(2) INFORMATION FOR SEQ ID NO: 4:

(i) SEQUENCE CHARACTERISTICS:
```

(A) LENGTH: 36 amino acids
                (B) TYPE: amino acid
                (D) TOPOLOGY: linear (ii) MOLECULE TYPE: protein (xi) SEQUENCE DESCRIPTION: SEQ ID NO: 4:

Gln Gln Thr Val Trp Gly Gln Cys Gly Gly Ile Gly Trp Ser Gly Pro
1               5                   10                  15

Thr Asn Cys Ala Pro Gly Ser Ala Cys Ser Thr Leu Asn Pro Tyr Tyr
            20                  25                  30

Ala Gln Cys Ile
        35

(2) INFORMATION FOR SEQ ID NO: 5:

(i) SEQUENCE CHARACTERISTICS:
                (A) LENGTH: 1201 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: CDS
                (B) LOCATION: join(1..704, 775..1201)

(xi) SEQUENCE DESCRIPTION: SEQ ID NO: 5:

```
CAG CAA CCG GGT ACC AGC ACC CCC GAG GTC CAT CCC AAG TTG ACA ACC        48
Gln Gln Pro Gly Thr Ser Thr Pro Glu Val His Pro Lys Leu Thr Thr
1               5                   10                  15

TAC AAG TGT ACA AAG TCC GGG GGG TGC GTG GCC CAG GAC ACC TCG GTG        96
Tyr Lys Cys Thr Lys Ser Gly Gly Cys Val Ala Gln Asp Thr Ser Val
            20                  25                  30

GTC CTT GAC TGG AAC TAC CGC TGG ATG CAC GAC GCA AAC TAC AAC TCG       144
Val Leu Asp Trp Asn Tyr Arg Trp Met His Asp Ala Asn Tyr Asn Ser
        35                  40                  45

TGC ACC GTC AAC GGC GGC GTC AAC ACC ACG CTC TGC CCT GAC GAG GCG       192
Cys Thr Val Asn Gly Gly Val Asn Thr Thr Leu Cys Pro Asp Glu Ala
50                  55                  60

ACC TGT GGC AAG AAC TGC TTC ATC GAG GGC GTC GAC TAC GCC GCC TCG       240
Thr Cys Gly Lys Asn Cys Phe Ile Glu Gly Val Asp Tyr Ala Ala Ser
65                  70                  75                  80

GGC GTC ACG ACC TCG GGC AGC AGC CTC ACC ATG AAC CAG TAC ATG CCC       288
Gly Val Thr Thr Ser Gly Ser Ser Leu Thr Met Asn Gln Tyr Met Pro
            85                  90                  95

AGC AGC TCT GGC GGC TAC AGC AGC GTC TCT CCT CGG CTG TAT CTC CTG       336
Ser Ser Ser Gly Gly Tyr Ser Ser Val Ser Pro Arg Leu Tyr Leu Leu
            100                 105                 110

GAC TCT GAC GGT GAG TAC GTG ATG CTG AAG CTC AAC GGC CAG GAG CTG       384
Asp Ser Asp Gly Glu Tyr Val Met Leu Lys Leu Asn Gly Gln Glu Leu
        115                 120                 125

AGC TTC GAC GTC GAC CTC TCT GCT CTG CCG TGT GGA GAG AAC GGC TCG       432
Ser Phe Asp Val Asp Leu Ser Ala Leu Pro Cys Gly Glu Asn Gly Ser
        130                 135                 140

CTC TAC CTG TCT CAG ATG GAC GAG AAC GGG GGC GCC AAC CAG TAT AAC       480
Leu Tyr Leu Ser Gln Met Asp Glu Asn Gly Gly Ala Asn Gln Tyr Asn
145                 150                 155                 160

ACG GCC GGT GCC AAC TAC GGG AGC GGC TAC TGC GAT GCT CAG TGC CCC       528
Thr Ala Gly Ala Asn Tyr Gly Ser Gly Tyr Cys Asp Ala Gln Cys Pro
                165                 170                 175

GTC CAG ACA TGG AGG AAC GGC ACC CTC AAC ACT AGC CAC CAG GGC TTC       576
```

```
                                                                                          624
TGC TGC AAC GAG ATG GAT ATC CTG GAG GGC AAC TCG AGG GCG AAT GCC
Cys Cys Asn Glu Met Asp Ile Leu Glu Gly Asn Ser Arg Ala Asn Ala
        195                 200                 205

672
TTG ACC CCT CAC TCT TGC ACG GCC ACG GCC TGC GAC TCT GCC GGT TGC
Leu Thr Pro His Ser Cys Thr Ala Thr Ala Cys Asp Ser Ala Gly Cys
        210                 215                 220

714
GGC TTC AAC CCC TAT GGC AGC GGC TAC AAA  AG GTGAGCCTGA
Gly Phe Asn Pro Tyr Gly Ser Gly Tyr Lys  Ser
225             230                 235

TGCCACTACT ACCCCTTTCC TGGCGCTCTC GCGGTTTTCC ATGCTGACAT GGTTTTCCAG            774

820
C TAC TAC GGC CCC GGA GAT ACC GTT GAC ACC TCC AAG ACC TTC ACC
  Tyr Tyr Gly Pro Gly Asp Thr Val Asp Thr Ser Lys Thr Phe Thr
                240                 245                 250

868
ATC ATC ACC CAG TTC AAC ACG GAC AAC GGC TCG CCC TCG GGC AAC CTT
Ile Ile Thr Gln Phe Asn Thr Asp Asn Gly Ser Pro Ser Gly Asn Leu
                255                 260                 265

916
GTG AGC ATC ACC CGC AAG TAC CAG CAA AAC GGC GTC GAC ATC CCC AGC
Val Ser Ile Thr Arg Lys Tyr Gln Gln Asn Gly Val Asp Ile Pro Ser
        270                 275                 280

964
GCC CAG CCC GGC GGC GAC ACC ATC TCG TCC TGC CCG TCC GCC TCA GCC
Ala Gln Pro Gly Gly Asp Thr Ile Ser Ser Cys Pro Ser Ala Ser Ala
        285                 290                 295

1012
TAC GGC GGC CTC GCC ACC ATG GGC AAG GCC CTG AGC AGC GGC ATG GTG
Tyr Gly Gly Leu Ala Thr Met Gly Lys Ala Leu Ser Ser Gly Met Val
        300                 305                 310

1060
CTC GTG TTC AGC ATT TGG AAC GAC AAC AGC CAG TAC ATG AAC TGG CTC
Leu Val Phe Ser Ile Trp Asn Asp Asn Ser Gln Tyr Met Asn Trp Leu
315             320                 325                 330

1108
GAC AGC GGC AAC GCC GGC CCC TGC AGC AGC ACC GAG GGC AAC CCA TCC
Asp Ser Gly Asn Ala Gly Pro Cys Ser Ser Thr Glu Gly Asn Pro Ser
                335                 340                 345

1156
AAC ATC CTG GCC AAC AAC CCC AAC ACG CAC GTC GTC TTC TCC AAC ATC
Asn Ile Leu Ala Asn Asn Pro Asn Thr His Val Val Phe Ser Asn Ile
        350                 355                 360

1201
CGC TGG GGA GAC ATT GGG TCT ACT ACG AAC TCG ACT GCG CCC CCG
Arg Trp Gly Asp Ile Gly Ser Thr Thr Asn Ser Thr Ala Pro Pro
        365                 370                 375

(2) INFORMATION FOR SEQ ID NO: 6:

(i) SEQUENCE CHARACTERISTICS:
        (A) LENGTH: 377 amino acids
        (B) TYPE: amino acid
        (D) TOPOLOGY: linear (ii) MOLECULE TYPE: protein (xi) SEQUENCE DESCRIPTION: SEQ ID NO: 6:

Gln Gln Pro Gly Thr Ser Thr Pro Glu Val His Pro Lys Leu Thr Thr
1               5                   10                  15

Tyr Lys Cys Thr Lys Ser Gly Gly Cys Val Ala Gln Asp Thr Ser Val
                20                  25                  30

Val Leu Asp Trp Asn Tyr Arg Trp Met His Asp Ala Asn Tyr Asn Ser
        35                  40                  45

Cys Thr Val Asn Gly Gly Val Asn Thr Thr Leu Cys Pro Asp Glu Ala
    50                  55                  60

Thr Cys Gly Lys Asn Cys Phe Ile Glu Gly Val Asp Tyr Ala Ala Ser
65                  70                  75                  80
```

```
Gly Val Thr Thr Ser Gly Ser Ser Leu Thr Met Asn Gln Tyr Met Pro
                    85                  90                  95

Ser Ser Ser Gly Gly Tyr Ser Ser Val Ser Pro Arg Leu Tyr Leu Leu
            100                 105                 110

Asp Ser Asp Gly Glu Tyr Val Met Leu Lys Leu Asn Gly Gln Glu Leu
        115                 120                 125

Ser Phe Asp Val Asp Leu Ser Ala Leu Pro Cys Gly Glu Asn Gly Ser
    130                 135                 140

Leu Tyr Leu Ser Gln Met Asp Glu Asn Gly Gly Ala Asn Gln Tyr Asn
145                 150                 155                 160

Thr Ala Gly Ala Asn Tyr Gly Ser Gly Tyr Cys Asp Ala Gln Cys Pro
                165                 170                 175

Val Gln Thr Trp Arg Asn Gly Thr Leu Asn Thr Ser His Gln Gly Phe
            180                 185                 190

Cys Cys Asn Glu Met Asp Ile Leu Glu Gly Asn Ser Arg Ala Asn Ala
        195                 200                 205

Leu Thr Pro His Ser Cys Thr Ala Thr Ala Cys Asp Ser Ala Gly Cys
    210                 215                 220

Gly Phe Asn Pro Tyr Gly Ser Gly Tyr Lys Ser Tyr Tyr Gly Pro Gly
225                 230                 235                 240

Asp Thr Val Asp Thr Ser Lys Thr Phe Thr Ile Ile Thr Gln Phe Asn
                245                 250                 255

Thr Asp Asn Gly Ser Pro Ser Gly Asn Leu Val Ser Ile Thr Arg Lys
            260                 265                 270

Tyr Gln Gln Asn Gly Val Asp Ile Pro Ser Ala Gln Pro Gly Gly Asp
        275                 280                 285

Thr Ile Ser Ser Cys Pro Ser Ala Ser Ala Tyr Gly Gly Leu Ala Thr
    290                 295                 300

Met Gly Lys Ala Leu Ser Ser Gly Met Val Leu Val Phe Ser Ile Trp
305                 310                 315                 320

Asn Asp Asn Ser Gln Tyr Met Asn Trp Leu Asp Ser Gly Asn Ala Gly
                325                 330                 335

Pro Cys Ser Ser Thr Glu Gly Asn Pro Ser Asn Ile Leu Ala Asn Asn
            340                 345                 350

Pro Asn Thr His Val Val Phe Ser Asn Ile Arg Trp Gly Asp Ile Gly
    355                 360                 365

Ser Thr Thr Asn Ser Thr Ala Pro Pro
370                 375

(2) INFORMATION FOR SEQ ID NO: 7:

(i) SEQUENCE CHARACTERISTICS:
        (A) LENGTH: 1157 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1..56, 231..1157)

(xi) SEQUENCE DESCRIPTION: SEQ ID NO: 7:

GGG GTC CGA TTT GCC GGC GTT AAC ATC GCG GGT TTT GAC TTT GGC TGT    48
Gly Val Arg Phe Ala Gly Val Asn Ile Ala Gly Phe Asp Phe Gly Cys
  1               5                  10                  15
```

```
ACC ACA   GA GTGAGTACCC TTGTTTCCTG GTGTTGCTGG CTGGTTGGGC              96
Thr Thr  Asp

GGGTATACAG CGAAGCGGAC GCAAGAACAC CGCCGGTCCG CCACCATCAA GATGTGGGTG    156

GTAAGCGGCG GTGTTTTGTA CAACTACCTG ACAGCTCACT CAGGAAATGA GAATTAATGG    216

AAGTCTTGTT ACAG T GGC ACT TGC GTT ACC TCG AAG GTT TAT CCT CCG        264
              Gly Thr Cys Val Thr Ser Lys Val Tyr Pro Pro
               20              25              30

TTG AAG AAC TTC ACC GGC TCA AAC AAC TAC CCC GAT GGC ATC GGC CAG      312
Leu Lys Asn Phe Thr Gly Ser Asn Asn Tyr Pro Asp Gly Ile Gly Gln
                35              40              45

ATG CAG CAC TTC GTC AAC GAG GAC GGG ATG ACT ATT TTC CGC TTA CCT      360
Met Gln His Phe Val Asn Glu Asp Gly Met Thr Ile Phe Arg Leu Pro
            50              55              60

GTC GGA TGG CAG TAC CTC GTC AAC AAC AAT TTG GGC GGC AAT CTT GAT      408
Val Gly Trp Gln Tyr Leu Val Asn Asn Asn Leu Gly Gly Asn Leu Asp
        65              70              75

TCC ACG AGC ATT TCC AAG TAT GAT CAG CTT GTT CAG GGG TGC CTG TCT      456
Ser Thr Ser Ile Ser Lys Tyr Asp Gln Leu Val Gln Gly Cys Leu Ser
    80              85              90

CTG GGC GCA TAC TGC ATC GTC GAC ATC CAC AAT TAT GCT CGA TGG AAC      504
Leu Gly Ala Tyr Cys Ile Val Asp Ile His Asn Tyr Ala Arg Trp Asn
95              100             105             110

GGT GGG ATC ATT GGT CAG GGC GGC CCT ACT AAT GCT CAA TTC ACG AGC      552
Gly Gly Ile Ile Gly Gln Gly Gly Pro Thr Asn Ala Gln Phe Thr Ser
                115             120             125

CTT TGG TCG CAG TTG GCA TCA AAG TAC GCA TCT CAG TCG AGG GTG TGG      600
Leu Trp Ser Gln Leu Ala Ser Lys Tyr Ala Ser Gln Ser Arg Val Trp
            130             135             140

TTC GGC ATC ATG AAT GAG CCC CAC GAC GTG AAC ATC AAC ACC TGG GCT      648
Phe Gly Ile Met Asn Glu Pro His Asp Val Asn Ile Asn Thr Trp Ala
        145             150             155

GCC ACG GTC CAA GAG GTT GTA ACC GCA ATC CGC AAC GCT GGT GCT ACG      696
Ala Thr Val Gln Glu Val Val Thr Ala Ile Arg Asn Ala Gly Ala Thr
    160             165             170

TCG CAA TTC ATC TCT TTG CCT GGA AAT GAT TGG CAA TCT GCT GGG GCT      744
Ser Gln Phe Ile Ser Leu Pro Gly Asn Asp Trp Gln Ser Ala Gly Ala
175             180             185             190

TTC ATA TCC GAT GGC AGT GCA GCC GCC CTG TCT CAA GTC ACG AAC CCG      792
Phe Ile Ser Asp Gly Ser Ala Ala Ala Leu Ser Gln Val Thr Asn Pro
                195             200             205

GAT GGG TCA ACA ACG AAT CTG ATT TTT GAC GTG CAC AAA TAC TTG GAC      840
Asp Gly Ser Thr Thr Asn Leu Ile Phe Asp Val His Lys Tyr Leu Asp
            210             215             220

TCA GAC AAC TCC GGT ACT CAC GCC GAA TGT ACT ACA AAT AAC ATT GAC      888
Ser Asp Asn Ser Gly Thr His Ala Glu Cys Thr Thr Asn Asn Ile Asp
        225             230             235

GGC GCC TTT TCT CCG CTT GCC ACT TGG CTC CGA CAG AAC AAT CGC CAG      936
Gly Ala Phe Ser Pro Leu Ala Thr Trp Leu Arg Gln Asn Asn Arg Gln
    240             245             250

GCT ATC CTG ACA GAA ACC GGT GGT GGC AAC GTT CAG TCC TGC ATA CAA      984
Ala Ile Leu Thr Glu Thr Gly Gly Gly Asn Val Gln Ser Cys Ile Gln
255             260             265             270

GAC ATG TGC CAG CAA ATC CAA TAT CTC AAC CAG AAC TCA GAT GTC TAT     1032
Asp Met Cys Gln Gln Ile Gln Tyr Leu Asn Gln Asn Ser Asp Val Tyr
                275             280             285

CTT GGC TAT GTT GGT TGG GGT GCC GGA TCA TTT GAT AGC ACG TAT GTC     1080
Leu Gly Tyr Val Gly Trp Gly Ala Gly Ser Phe Asp Ser Thr Tyr Val
            290             295             300
```

```
CTG ACG GAA ACA CCG ACT AGC AGT GGT AAC TCA TGG ACG GAC ACA TCC    1128
Leu Thr Glu Thr Pro Thr Ser Ser Gly Asn Ser Trp Thr Asp Thr Ser
    305                 310                 315

TTG GTC AGC TCG TGT CTC GCA AGA AAG TA                             1157
Leu Val Ser Ser Cys Leu Ala Arg Lys
320                 325
```

(2) INFORMATION FOR SEQ ID NO: 8:

(i) SEQUENCE CHARACTERISTICS:
        (A) LENGTH: 327 amino acids
        (B) TYPE: amino acid
        (D) TOPOLOGY: linear (ii) MOLECULE TYPE: protein (xi) SEQUENCE DESCRIPTION: SEQ ID NO: 8:

```
Gly Val Arg Phe Ala Gly Val Asn Ile Ala Gly Phe Asp Phe Gly Cys
 1               5                  10                  15

Thr Thr Asp Gly Thr Cys Val Thr Ser Lys Val Tyr Pro Pro Leu Lys
                20                  25                  30

Asn Phe Thr Gly Ser Asn Asn Tyr Pro Asp Gly Ile Gly Gln Met Gln
            35                  40                  45

His Phe Val Asn Glu Asp Gly Met Thr Ile Phe Arg Leu Pro Val Gly
    50                  55                  60

Trp Gln Tyr Leu Val Asn Asn Leu Gly Gly Asn Leu Asp Ser Thr
65                  70                  75                  80

Ser Ile Ser Lys Tyr Asp Gln Leu Val Gln Gly Cys Leu Ser Leu Gly
                85                  90                  95

Ala Tyr Cys Ile Val Asp Ile His Asn Tyr Ala Arg Trp Asn Gly Gly
                100                 105                 110

Ile Ile Gly Gln Gly Gly Pro Thr Asn Ala Gln Phe Thr Ser Leu Trp
            115                 120                 125

Ser Gln Leu Ala Ser Lys Tyr Ala Ser Gln Ser Arg Val Trp Phe Gly
130                 135                 140

Ile Met Asn Glu Pro His Asp Val Asn Ile Asn Thr Trp Ala Ala Thr
145                 150                 155                 160

Val Gln Glu Val Val Thr Ala Ile Arg Asn Ala Gly Ala Thr Ser Gln
                165                 170                 175

Phe Ile Ser Leu Pro Gly Asn Asp Trp Gln Ser Ala Gly Ala Phe Ile
            180                 185                 190

Ser Asp Gly Ser Ala Ala Leu Ser Gln Val Thr Asn Pro Asp Gly
        195                 200                 205

Ser Thr Thr Asn Leu Ile Phe Asp Val His Lys Tyr Leu Asp Ser Asp
    210                 215                 220

Asn Ser Gly Thr His Ala Glu Cys Thr Thr Asn Asn Ile Asp Gly Ala
225                 230                 235                 240

Phe Ser Pro Leu Ala Thr Trp Leu Arg Gln Asn Asn Arg Gln Ala Ile
                245                 250                 255

Leu Thr Glu Thr Gly Gly Gly Asn Val Gln Ser Cys Ile Gln Asp Met
            260                 265                 270

Cys Gln Gln Ile Gln Tyr Leu Asn Gln Asn Ser Asp Val Tyr Leu Gly
        275                 280                 285

Tyr Val Gly Trp Gly Ala Gly Ser Phe Asp Ser Thr Tyr Val Leu Thr
    290                 295                 300

Glu Thr Pro Thr Ser Ser Gly Asn Ser Trp Thr Asp Thr Ser Leu Val
305                 310                 315                 320
```

Ser Ser Cys Leu Ala Arg Lys
            325

(2) INFORMATION FOR SEQ ID NO: 9:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..81

(xi) SEQUENCE DESCRIPTION: SEQ ID NO: 9:

CCC CCG CCT GCG TCC AGC ACG ACG TTT TCG ACT ACA CCG AGG AGC TCG        48
Pro Pro Pro Ala Ser Ser Thr Thr Phe Ser Thr Thr Pro Arg Ser Ser
 1               5                  10                  15

ACG ACT TCG AGC AGC CCG AGC TGC ACG CAG ACT                            81
Thr Thr Ser Ser Ser Pro Ser Cys Thr Gln Thr
            20                  25

(2) INFORMATION FOR SEQ ID NO: 10:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO: 10:

Pro Pro Pro Ala Ser Ser Thr Thr Phe Ser Thr Thr Pro Arg Ser Ser
 1               5                  10                  15

Thr Thr Ser Ser Ser Pro Ser Cys Thr Gln Thr
            20                  25

(2) INFORMATION FOR SEQ ID NO: 11:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..102

(xi) SEQUENCE DESCRIPTION: SEQ ID NO: 11:

CCG GGA GCC ACT ACT ATC ACC ACT TCG ACC CGG CCA CCA TCC GGT CCA        48
Pro Gly Ala Thr Thr Ile Thr Thr Ser Thr Arg Pro Pro Ser Gly Pro
 1               5                  10                  15

ACC ACC ACC ACC AGG GCT ACC TCA ACA AGC TCA TCA ACT CCA CCC ACG        96
Thr Thr Thr Thr Arg Ala Thr Ser Thr Ser Ser Ser Thr Pro Pro Thr
            20                  25                  30

AGC TCT                                                               102
Ser Ser (2) INFORMATION FOR SEQ ID NO: 12:

(i) SEQUENCE CHARACTERISTICS:

```
            (A) LENGTH: 34 amino acids
            (B) TYPE: amino acid
            (D) TOPOLOGY: linear (ii) MOLECULE TYPE: protein (xi) SEQUENCE DESCRIPTION: SEQ ID NO: 12:

Pro Gly Ala Thr Thr Ile Thr Thr Ser Thr Arg Pro Pro Ser Gly Pro
 1               5                  10                  15

Thr Thr Thr Thr Arg Ala Thr Ser Thr Ser Ser Ser Thr Pro Pro Thr
                20                  25                  30

Ser Ser (2) INFORMATION FOR SEQ ID NO: 13:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..66

(xi) SEQUENCE DESCRIPTION: SEQ ID NO: 13:

ATG GCG CCC TCA GTT ACA CTG CCG TTG ACC ACG GCC ATC CTG GCC ATT         48
Met Ala Pro Ser Val Thr Leu Pro Leu Thr Thr Ala Ile Leu Ala Ile
 1               5                  10                  15

GCC CGG CTC GTC GCC GCC                                                 66
Ala Arg Leu Val Ala Ala
                20

(2) INFORMATION FOR SEQ ID NO: 14:

(i) SEQUENCE CHARACTERISTICS:
            (A) LENGTH: 22 amino acids
            (B) TYPE: amino acid
            (D) TOPOLOGY: linear (ii) MOLECULE TYPE: protein (xi) SEQUENCE DESCRIPTION: SEQ ID NO: 14:

Met Ala Pro Ser Val Thr Leu Pro Leu Thr Thr Ala Ile Leu Ala Ile
 1               5                  10                  15

Ala Arg Leu Val Ala Ala
                20

(2) INFORMATION FOR SEQ ID NO: 15:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..63

(xi) SEQUENCE DESCRIPTION: SEQ ID NO: 15:

ATG AAC AAG TCC GTG GCT CCA TTG CTG CTT GCA GCG TCC ATA CTA TAT         48
Met Asn Lys Ser Val Ala Pro Leu Leu Leu Ala Ala Ser Ile Leu Tyr
 1               5                  10                  15
```

```
GGC GGC GCC GTC GCA                                                        63
Gly Gly Ala Val Ala
            20

(2) INFORMATION FOR SEQ ID NO: 16:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO: 16:

Met Asn Lys Ser Val Ala Pro Leu Leu Leu Ala Ala Ser Ile Leu Tyr
 1               5                  10                  15

Gly Gly Ala Val Ala
            20

(2) INFORMATION FOR SEQ ID NO: 17:

(i) SEQUENCE CHARACTERISTICS:
        (A) LENGTH: 777 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

AAACCAGCTG TGACCAGTGG GCAACCTTCA CTGGCAACGG CTACACAGTC AGCAACAACC    60

TTTGGGGAGC ATCAGCCGGC TCTGGATTTG GCTGCGTGAC GGCGGTATCG CTCAGCGGCG   120

GGGCCTCCTG GCACGCAGAC TGGCAGTGGT CCGGCGGCCA GAACAACGTC AAGTCGTACC   180

AGAACTCTCA GATTGCCATT CCCCAGAAGA GGACCGTCAA CAGCATCAGC AGCATGCCCA   240

CCACTGCCAG CTGGAGCTAC AGCGGGAGCA ACATCCGCGC TAATGTTGCG TATGACTTGT   300

TCACCGCAGC CAACCCGAAT CATGTCACGT ACTCGGGAGA CTACGAACTC ATGATCTGGT   360

AAGCCATAAG AAGTGACCCT CCTTGATAGT TTCGACTAAC AACATGTCTT GAGGCTTGGC   420

AAATACGGCG ATATTGGGCC GATTGGGTCC TCACAGGGAA CAGTCAACGT CGGTGGCCAG   480

AGCTGGACGC TCTACTATGG CTACAACGGA GCCATGCAAG TCTATTCCTT TGTGGCCCAG   540

ACCAACACTA CCAACTACAG CGGAGATGTC AAGAACTTCT TCAATTATCT CCGAGACAAT   600

AAAGGATACA ACGCTGCAGG CCAATATGTT CTTAGTAAGT CACCCTCACT GTGACTGGGC   660

TGAGTTTGTT GCAACGTTTG CTAACAAAAC CTTCGTATAG GCTACCAATT TGGTACCGAG   720

CCCTTCACGG GCAGTGGAAC TCTGAACGTC GCATCCTGGA CCGCATCTAT CAACTAA     777

(2) INFORMATION FOR SEQ ID NO: 18:

(i) SEQUENCE CHARACTERISTICS:
        (A) LENGTH: 218 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 18:

Gln Thr Ser Cys Asp Gln Trp Ala Thr Phe Thr Gly Asn Gly Tyr Thr
 1               5                  10                  15

Val Ser Asn Asn Leu Trp Gly Ala Ser Ala Gly Ser Gly Phe Gly Cys
```

```
              20                  25                  30
Val Thr Ala Val Ser Leu Ser Gly Gly Ala Ser Trp His Ala Asp Trp
                35                  40                  45
Gln Trp Ser Gly Gly Gln Asn Asn Val Lys Ser Tyr Gln Asn Ser Gln
 50                  55                  60
Ile Ala Ile Pro Gln Lys Arg Thr Val Asn Ser Ile Ser Ser Met Pro
 65                  70                  75                  80
Thr Thr Ala Ser Trp Ser Tyr Ser Gly Ser Asn Ile Arg Ala Asn Val
                 85                  90                  95
Ala Tyr Asp Leu Phe Thr Ala Ala Asn Pro Asn His Val Thr Tyr Ser
                100                 105                 110
Gly Asp Tyr Glu Leu Met Ile Trp Leu Gly Lys Tyr Gly Asp Ile Gly
                115                 120                 125
Pro Ile Gly Ser Ser Gln Gly Thr Val Asn Val Gly Gly Gln Ser Trp
130                 135                 140
Thr Leu Tyr Tyr Gly Tyr Asn Gly Ala Met Gln Val Tyr Ser Phe Val
145                 150                 155                 160
Ala Gln Thr Asn Thr Thr Asn Tyr Ser Gly Asp Val Lys Asn Phe Phe
                165                 170                 175
Asn Tyr Leu Arg Asp Asn Lys Gly Tyr Asn Ala Ala Gly Gln Tyr Val
                180                 185                 190
Leu Ser Tyr Gln Phe Gly Thr Glu Pro Phe Thr Gly Ser Gly Thr Leu
                195                 200                 205
Asn Val Ala Ser Trp Thr Ala Ser Ile Asn
                210                 215

(2) INFORMATION FOR SEQ ID NO: 19:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

ATGAAGTTCC TTCAAGTCCT CCCTGCCCTC ATACCGGCCG CCCTGGCCC            49

(2) INFORMATION FOR SEQ ID NO: 20:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Met Lys Phe Leu Gln Val Leu Pro Ala Leu Ile Pro Ala Ala Leu Ala
 1               5                  10                  15

(2) INFORMATION FOR SEQ ID NO: 21:

(i) SEQUENCE CHARACTERISTICS:
        (A) LENGTH: 57 base pairs
        (B) TYPE: nucleic acid
        (C) STRANDEDNESS: double
        (D) TOPOLOGY: linear
```

-continued (xi) SEQUENCE DESCRIPTION: SEQ ID NO: 21:

AGCTCGTAGA GCGTTGACTT GCCTGTGGTC TGTCCAGACG GGGGACGATA GAATGCG    57